(12) United States Patent
Peterson et al.

(10) Patent No.: US 10,946,177 B2
(45) Date of Patent: Mar. 16, 2021

(54) GUIDE EXTENSION CATHETER

(71) Applicant: Teleflex Life Sciences Limited, Valletta (MT)

(72) Inventors: Dean Peterson, Minneapolis, MN (US); Joshua Brenizer, Oak Grove, MN (US)

(73) Assignee: Teleflex Life Sciences Limited, Valletta (MT)

( * ) Notice: Subject to any disclaimer, the term of this patent is extended or adjusted under 35 U.S.C. 154(b) by 0 days.

(21) Appl. No.: 16/643,759

(22) PCT Filed: Oct. 30, 2019

(86) PCT No.: PCT/US2019/058786
§ 371 (c)(1),
(2) Date: Mar. 2, 2020

(87) PCT Pub. No.: WO2020/131227
PCT Pub. Date: Jun. 25, 2020

(65) Prior Publication Data
US 2021/0008355 A1 Jan. 14, 2021

Related U.S. Application Data

(60) Provisional application No. 62/781,973, filed on Dec. 19, 2018.

(51) Int. Cl.
*A61M 25/10* (2013.01)
*A61M 39/06* (2006.01)

(52) U.S. Cl.
CPC ...... *A61M 25/1025* (2013.01); *A61M 25/104* (2013.01); *A61M 39/06* (2013.01);
(Continued)

(58) Field of Classification Search
CPC .............. A61M 25/0138; A61M 39/06; A61M 25/0102; A61M 2025/0047; A61M 2210/125
See application file for complete search history.

(56) References Cited

U.S. PATENT DOCUMENTS

| 4,000,739 A | 1/1977 | Stevens |
| 4,166,468 A | 9/1979 | Haynie |

(Continued)

FOREIGN PATENT DOCUMENTS

| CA | 2008784 C | 7/2002 |
| DE | 69928825 | 7/2006 |

(Continued)

OTHER PUBLICATIONS

Bertrand, Michel E. "The Evolution of Cardiac Catheterization and Interventional Cardiology," European Society of Cardiology, 2006, 10 pages.

(Continued)

*Primary Examiner* — Amber R Stiles
(74) *Attorney, Agent, or Firm* — Robert B. Madden; Gregory W. Smock

(57) ABSTRACT

This patent document discloses guide extension catheters for use with a predefined length guide catheter and related methods for treating blood vessel lesions and abnormalities. A guide extension catheter can include a push member, an elongate tube member, and a balloon radially surrounding a portion of the elongate tube member. The balloon can include an inflatable tube coupled to an elongate shaft having a lumen for receiving inflation fluid, and the inflatable tube can be coiled in a helical manner around the elongate tube member. A bioactive layer can coat an outer surface portion of the balloon and, when the balloon is inflated, one or more drugs of the bioactive layer can be received by the blood vessel. Inflation of the balloon can engage the elongate tube member with an inner surface of the blood vessel and/or an inner surface of the guide catheter.

20 Claims, 13 Drawing Sheets

(52) U.S. Cl.
CPC . *A61M 25/10181* (2013.11); *A61M 2025/105* (2013.01); *A61M 2025/1061* (2013.01); *A61M 2025/1075* (2013.01); *A61M 2039/062* (2013.01)

(56) References Cited

U.S. PATENT DOCUMENTS

| | | |
|---|---|---|
| 4,289,128 A | 9/1981 | Rusch |
| 4,723,936 A | 2/1988 | Buchbinder et al. |
| 4,762,129 A | 8/1988 | Bonzel |
| 4,762,130 A | 8/1988 | Fogarty et al. |
| 4,813,930 A | 3/1989 | Elliott |
| 4,832,028 A | 5/1989 | Patel |
| 4,838,268 A | 6/1989 | Keith et al. |
| 4,838,269 A | 6/1989 | Robinson et al. |
| 4,909,252 A | 3/1990 | Goldberger |
| 4,921,483 A | 5/1990 | Wijay et al. |
| 4,932,413 A | 6/1990 | Shockey et al. |
| 4,943,278 A | 7/1990 | Euteneuer et al. |
| 4,946,440 A | 8/1990 | Hall |
| 4,994,745 A | 2/1991 | Mizuta |
| 5,002,531 A | 3/1991 | Bonzel |
| 5,040,548 A | 8/1991 | Yock |
| 5,061,273 A | 10/1991 | Yock |
| 5,074,845 A | 12/1991 | Miraki et al. |
| 5,098,412 A | 3/1992 | Shiu |
| 5,102,403 A | 4/1992 | Alt |
| 5,120,323 A | 6/1992 | Shockey et al. |
| 5,122,125 A | 6/1992 | Deuss |
| 5,156,594 A | 10/1992 | Keith |
| 5,226,888 A | 7/1993 | Arney |
| 5,232,445 A | 8/1993 | Bonzel |
| 5,234,416 A | 8/1993 | Macaulay et al. |
| 5,257,974 A | 11/1993 | Cox |
| 5,267,958 A | 12/1993 | Buchbinder et al. |
| 5,290,247 A | 3/1994 | Crittenden |
| 5,328,472 A | 7/1994 | Steinke et al. |
| 5,344,401 A | 9/1994 | Radisch et al. |
| 5,350,395 A | 9/1994 | Yock |
| 5,368,567 A | 11/1994 | Lee |
| 5,383,853 A | 1/1995 | Jung et al. |
| 5,395,389 A | 3/1995 | Patel |
| 5,413,560 A | 5/1995 | Solar |
| 5,415,639 A | 5/1995 | VandenEinde et al. |
| 5,439,445 A | 8/1995 | Kontos |
| 5,441,489 A | 8/1995 | Utsumi et al. |
| 5,445,624 A | 8/1995 | Jimenez |
| 5,445,625 A | 8/1995 | Voda |
| 5,451,209 A | 9/1995 | Ainsworth et al. |
| 5,472,425 A | 12/1995 | Teirstein |
| 5,484,409 A | 1/1996 | Atkinson et al. |
| 5,489,278 A | 2/1996 | Abrahamson |
| 5,527,292 A | 6/1996 | Adams et al. |
| 5,531,721 A | 7/1996 | Pepin et al. |
| 5,545,149 A | 8/1996 | Brin et al. |
| 5,549,553 A | 8/1996 | Ressemann et al. |
| 5,562,620 A | 10/1996 | Klein et al. |
| 5,567,203 A | 10/1996 | Euteneuer et al. |
| 5,571,087 A | 11/1996 | Ressemann et al. |
| 5,578,009 A | 11/1996 | Kraus et al. |
| 5,599,326 A | 2/1997 | Carter |
| 5,620,417 A | 4/1997 | Jang et al. |
| 5,649,909 A | 7/1997 | Cornelius |
| 5,658,263 A | 8/1997 | Dang et al. |
| 5,658,309 A | 8/1997 | Berthiaume et al. |
| 5,690,613 A | 11/1997 | Verbeek |
| 5,704,926 A | 1/1998 | Sutton |
| 5,720,300 A | 2/1998 | Fagan et al. |
| 5,720,724 A | 2/1998 | Ressemann et al. |
| 5,743,876 A | 4/1998 | Swanson |
| 5,772,642 A | 6/1998 | Ciamacco et al. |
| 5,776,141 A | 7/1998 | Klein et al. |
| 5,785,685 A | 7/1998 | Kugler et al. |
| 5,792,124 A | 8/1998 | Horrigan et al. |
| 5,843,022 A | 12/1998 | Willard et al. |
| 5,860,963 A | 1/1999 | Azam et al. |
| 5,891,056 A | 4/1999 | Ramzipoor |
| 5,902,290 A | 5/1999 | Peacock et al. |
| 5,911,715 A | 6/1999 | Berg et al. |
| 5,961,510 A | 10/1999 | Fugoso et al. |
| 5,980,486 A | 11/1999 | Enger |
| 6,042,578 A | 3/2000 | Dinh et al. |
| 6,071,273 A | 6/2000 | Euteneuer et al. |
| 6,102,890 A | 8/2000 | Stivland et al. |
| 6,159,195 A | 12/2000 | Ha et al. |
| 6,190,358 B1 | 2/2001 | Fitzmaurice et al. |
| 6,193,686 B1 | 2/2001 | Estrada et al. |
| 6,199,262 B1 | 3/2001 | Martin |
| 6,270,465 B1 | 8/2001 | Keith et al. |
| 6,299,628 B1 | 10/2001 | Harrison et al. |
| 6,338,725 B1 | 1/2002 | Hermann et al. |
| 6,398,773 B1 | 6/2002 | Bagaoisan et al. |
| 6,409,863 B1 | 6/2002 | Williams et al. |
| 6,443,912 B1 | 9/2002 | Mazzola et al. |
| 6,475,195 B1 | 11/2002 | Voda |
| 6,488,655 B1 | 12/2002 | Wantink et al. |
| 6,503,223 B1 | 1/2003 | Sekido et al. |
| 6,503,353 B1 | 1/2003 | Peterson et al. |
| 6,548,010 B1 | 4/2003 | Stivland et al. |
| 6,575,958 B1 | 6/2003 | Happ et al. |
| 6,591,472 B1 | 7/2003 | Noone et al. |
| 6,595,952 B2 | 7/2003 | Forsberg |
| 6,610,068 B1 | 8/2003 | Yang |
| 6,620,149 B1 | 9/2003 | Lenz et al. |
| 6,635,029 B1 | 10/2003 | Venturelli |
| 6,638,268 B2 | 10/2003 | Niazi |
| 6,648,874 B2 | 11/2003 | Parisi et al. |
| 6,689,144 B2 | 2/2004 | Gerberding |
| 6,706,018 B2 | 3/2004 | Westlund et al. |
| 6,733,487 B2 | 5/2004 | Keith et al. |
| 6,755,812 B2 | 6/2004 | Peterson et al. |
| 6,860,876 B2 | 3/2005 | Chen |
| 6,997,908 B2 | 2/2006 | Carrillo, Jr. et al. |
| 7,169,162 B2 | 1/2007 | Garakani |
| 7,232,452 B2 | 6/2007 | Adams et al. |
| 7,294,124 B2 | 11/2007 | Eidenschink |
| 7,374,560 B2 | 5/2008 | Ressemann et al. |
| 7,422,579 B2 | 9/2008 | Wahr et al. |
| 7,544,201 B2 | 6/2009 | Pepper |
| 7,604,612 B2 | 10/2009 | Ressemann et al. |
| 7,697,996 B2 | 4/2010 | Manning et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 7,763,012 B2 | 7/2010 | Petrick et al. |
| 7,959,603 B2 | 6/2011 | Wahr et al. |
| 8,048,032 B2 | 11/2011 | Root et al. |
| 8,142,413 B2 | 3/2012 | Root et al. |
| 8,292,850 B2 | 10/2012 | Root et al. |
| 8,292,872 B2 | 10/2012 | Soetermans |
| 8,414,909 B2 | 4/2013 | Wang |
| 8,613,722 B2 | 12/2013 | Lee et al. |
| 8,721,624 B2 | 5/2014 | Wilson et al. |
| 8,814,890 B2 | 8/2014 | Miyata et al. |
| RE45,380 E | 2/2015 | Root et al. |
| 8,996,095 B2 | 3/2015 | Anderson et al. |
| 9,144,662 B2 | 9/2015 | Caprio et al. |
| RE45,760 E | 10/2015 | Root et al. |
| RE45,776 E | 10/2015 | Root et al. |
| RE46,116 E | 8/2016 | Root et al. |
| 9,655,998 B2 | 5/2017 | Gemborys |
| 9,968,763 B2 | 5/2018 | Root et al. |
| 10,173,029 B2 | 1/2019 | Webster et al. |
| RE47,379 E | 5/2019 | Root et al. |
| 10,751,514 B2 | 8/2020 | Brenizer et al. |
| 2001/0016712 A1 | 8/2001 | Hamilton |
| 2002/0165598 A1* | 11/2002 | Wahr ............... A61B 17/12045 623/1.11 |
| 2003/0195546 A1 | 10/2003 | Solar et al. |
| 2003/0233117 A1 | 12/2003 | Adams et al. |
| 2004/0010280 A1 | 1/2004 | Adams et al. |
| 2004/0127927 A1 | 7/2004 | Adams |
| 2004/0236215 A1 | 11/2004 | Mihara et al. |
| 2005/0004523 A1 | 1/2005 | Osborne et al. |

(56) References Cited

U.S. PATENT DOCUMENTS

| | | |
|---|---|---|
| 2005/0015073 A1 | 1/2005 | Kataishi et al. |
| 2005/0182437 A1 | 8/2005 | Bonnette et al. |
| 2006/0247661 A1 | 11/2006 | Richards et al. |
| 2007/0260219 A1 | 11/2007 | Root et al. |
| 2008/0082045 A1 | 4/2008 | Goldfarb et al. |
| 2008/0243171 A1 | 10/2008 | Ressemann et al. |
| 2009/0005755 A1 | 1/2009 | Keith et al. |
| 2009/0264865 A1 | 10/2009 | Kawai |
| 2009/0285974 A1* | 11/2009 | Kerrigan ............. A61L 31/14 427/2.21 |
| 2009/0299327 A1* | 12/2009 | Tilson ............. A61M 25/0147 604/500 |
| 2012/0296313 A1 | 11/2012 | Andreacchi et al. |
| 2013/0072904 A1 | 3/2013 | Musbach et al. |
| 2013/0116701 A1 | 5/2013 | Wang et al. |
| 2013/0197483 A1 | 8/2013 | Anderson et al. |
| 2014/0012281 A1 | 1/2014 | Wang et al. |
| 2014/0018773 A1 | 1/2014 | Wang et al. |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0052097 A1 | 2/2014 | Petersen et al. |
| 2014/0081243 A1 | 3/2014 | Zhou et al. |
| 2014/0142506 A1 | 5/2014 | Prindle et al. |
| 2014/0171914 A1 | 6/2014 | Rowe et al. |
| 2014/0249508 A1 | 9/2014 | Wang et al. |
| 2014/0276618 A1 | 9/2014 | Di Caprio et al. |
| 2014/0358123 A1 | 12/2014 | Ueda et al. |
| 2015/0051633 A1 | 2/2015 | Sina |
| 2015/0151090 A1 | 6/2015 | Sutton et al. |
| 2016/0008572 A1 | 1/2016 | Caprio et al. |
| 2016/0051799 A1 | 2/2016 | Daniels et al. |
| 2016/0066932 A1 | 3/2016 | Root et al. |
| 2016/0346515 A1 | 12/2016 | Buller et al. |
| 2018/0161547 A1 | 6/2018 | Brenizer et al. |
| 2020/0054865 A1 | 2/2020 | Bridgeman et al. |
| 2021/0008342 A1 | 1/2021 | Buller et al. |
| 2021/0008343 A1 | 1/2021 | Brenizer et al. |

FOREIGN PATENT DOCUMENTS

| | | |
|---|---|---|
| EP | 0313558 B1 | 1/1991 |
| EP | 0380873 B1 | 5/1994 |
| EP | 0365993 B1 | 12/1994 |
| EP | 0881921 A1 | 12/1998 |
| EP | 1084728 A1 | 3/2001 |
| EP | 0992260 B1 | 9/2007 |
| JP | H10507095 A | 7/1998 |
| JP | 2004275435 A | 10/2004 |
| JP | 2012135379 A | 7/2012 |
| WO | 1984003633 A1 | 9/1984 |
| WO | 1996001604 A1 | 1/1996 |
| WO | 1997037713 A1 | 10/1997 |
| WO | 1999048548 A1 | 9/1999 |
| WO | 2000024451 A9 | 11/2000 |
| WO | 2014028898 A2 | 2/2014 |
| WO | 2016191415 A1 | 12/2016 |
| WO | 2017019900 A1 | 2/2017 |

OTHER PUBLICATIONS

Bonzel, T. et al. "The Sliding Rail System (Monorail): Description of a New Technique for Intravascular Instrumentation and its Application to Coronary Angioplasty," Z. Kardiol. 76, Supp. 6 (1987), pp. 119-122.

Iqbal et al. "Coronary stents: historical development, current status and future directions," British Medical Bulletin, 2013, 106: 193-211.

PCT International Search Report and Written Opinion dated Jan. 10, 2020 in PCT Application No. PCT/US2019/058786.

Takahashi, Saeko. "New Method to Increase a Backup Support of a 6 French Guiding Coronary Catheter," Catheterization and Cardiovascular Interventions 63:452-456 (2004), 5 pages, published online in Wiley InterScience (www.interscience.wiley.com).

Topol, Eric J. "Textbook of Interventional Cardiology," Saunders Elseveir, 5th Edition, 2008, p. 277-280.

Tully, Shawn. "Blood Feud This little piece of metal is worth $4.5 billion this year, generates more profits than a blockbuster drug, and has sparked one of the weirdest corporate battles ever. It could also save your life." CNN Money, May 31, 2004, 5 pages. Retrieved Jan. 14, 2019 on the Internet: <https://money.cnn.com/magazines/fortune/fortune_archive/2004/05/31/370693/index.htm>.

Vascular Solutions, Inc. "GuideLiner V3 catheter: Guide Extension Catheter with Half-Pipe Technology" [Brochure], Dec. 2013, Minneapolis, MN.

\* cited by examiner

GUIDE EXTENSION CATHETER

CLAIM OF PRIORITY

This application is a national stage application under 35 U.S.C. 371 of PCT Application No. PCT/US2019/058786, filed Oct. 30, 2019, which claims priority to U.S. provisional patent application Ser. No. 62/781,973, entitled "GUIDE EXTENSION CATHETER" and filed on Dec. 19, 2018, both of which are herein incorporated by reference in their entirety.

TECHNICAL FIELD

The subject matter of this patent document relates to the field of medical devices. More particularly, but not by way of limitation, the subject matter relates to guide extension catheters for use with guide catheters.

BACKGROUND

Interventional cardiology procedures often involve inserting guidewires or other instruments through catheters into coronary arteries that branch off from the aorta. In coronary artery disease, a coronary artery may be narrowed or occluded by atherosclerotic plaques or other lesions. These lesions may totally obstruct the lumen of the artery or may dramatically narrow the lumen of the artery. Narrowing is referred to as stenosis. In order to diagnose and treat obstructive coronary artery disease, it is commonly necessary to pass a guidewire or other instruments through and beyond the occlusion or stenosis of the coronary artery.

To treat a stenosis, a guide catheter can be inserted through the aorta and into the ostium of the coronary artery. This is sometimes accomplished with the aid of the guidewire. The guide catheter is typically seated into the opening or ostium of the artery to be treated and the guidewire or other instrument is passed through the lumen of the guide catheter and inserted into the artery beyond the occlusion or stenosis. Crossing tough lesions or tortuous anatomy can create enough backward force to dislodge the guide catheter from the ostium of the artery being treated. This can make it difficult or impossible for the interventional cardiologist to treat certain forms of coronary artery disease.

A coaxial guide catheter can be used in conjunction with a standard guide catheter to provide additional backup support. The coaxial guide catheter can be passed through the standard guide catheter until its distal end extends beyond the distal end of the standard guide catheter, thereby positioning the distal end of the coaxial guide catheter further within the branch artery harboring the stenosis. Coaxial guide catheters may thus be referred to as guide extension catheters.

Holding guide extension catheters in place during an operation can be difficult, especially when multiple interventional devices are employed simultaneously. Movement of the guide extension catheter may result in one or more instruments becoming dislodged from the treatment site, which may be difficult to re-access. Accordingly, new devices or techniques capable of increasing the back-up support for guide extension catheters positioned at a target site are needed.

OVERVIEW

The present inventors recognize that there is a need to provide guide extension catheters that are compatible with guide catheters for performing interventional procedures in challenging anatomy, e.g., narrow blood vessels harboring robust occlusions. The present inventors also recognize that there is a need to provide increased back-up support to interventional devices and guide catheters during interventional procedures. A guide extension catheter that includes guide extension tubing at least partially surrounded by a balloon can be used in conjunction with a guide catheter to access discrete regions of coronary or peripheral vasculature and to facilitate accurate placement of interventional devices without guide catheter back-out from a vessel ostium or branch of interest.

Guide extension catheters and related methods are disclosed in this patent document. A guide extension catheter can comprise an elongate tube member (also referred to as guide extension tubing) and a push member (also referred to as a substantially rigid portion). A balloon can envelope or surround at least a portion of the elongate tube member, such that upon its inflation, an outer surface of the balloon may contact, and exert an outward pressure on, an inner surface of a blood vessel and/or the guide catheter, thereby securing the tube member within the vessel and/or the guide catheter. The balloon can optionally be coated with a bioactive layer including one or more drugs and excipients for treatment of the blood vessel. The push member can be eccentrically coupled to the tube member for slidably positioning the tube member within and partially beyond a distal end of a guide catheter and a vessel ostium of interest.

These and other embodiments and features of the present guide extension catheters and related methods will be set forth, at least in part, in the following Detailed Description. This Overview is intended to provide non-limiting embodiments of the present subject matter; it is not intended to provide an exclusive or exhaustive explanation of the disclosed embodiments. The Detailed Description below is included to provide further information about the present guide extension catheters and methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in this patent document.

The drawings are not necessarily to scale. Certain features and components may be shown exaggerated in scale or in schematic form, and some details may not be shown in the interest of clarity and conciseness.

DETAILED DESCRIPTION

This patent document discloses guide extension catheters to be placed within guide catheters for providing support and guidance in a vessel when percutaneously advancing interventional devices, such as guidewires, balloon catheters, stents or stent catheters. A guide extension catheter is configured to be passed through a main lumen of a guide catheter so that its distal end portion can be extended past a distal end of the guide catheter and into the desired vessel while its intermediate portions remain within the guide catheter, for example as described in commonly-owned U.S. Pat. Nos. 8,048,032, 8,142,413, RE45,760, RE45,380, RE45,776, and RE46,116, which are incorporated by reference in their entireties herein. The guide extension catheter improves the ability of the guide catheter to remain seated in the desired vessel's ostium or branch during an interventional procedure. A balloon coupled to the elongate tube member at a distal portion of the guide extension catheter provides increased back-up support for the guide extension catheter during use, thereby simplifying manipulation of the guide extension catheter.

It is believed that the present guide extension catheters will find great utility by interventional cardiologists performing percutaneous transluminal coronary interventions. Although the remainder of this patent document generally discusses and illustrates such uses, it should be understood that the guide extension catheters can also be used for treating other non-coronary diseased vessels or other hollow structures (e.g., biliary tract, ureter, etc.) throughout a patient's body where interventional devices are or can be employed.

Figure 1:
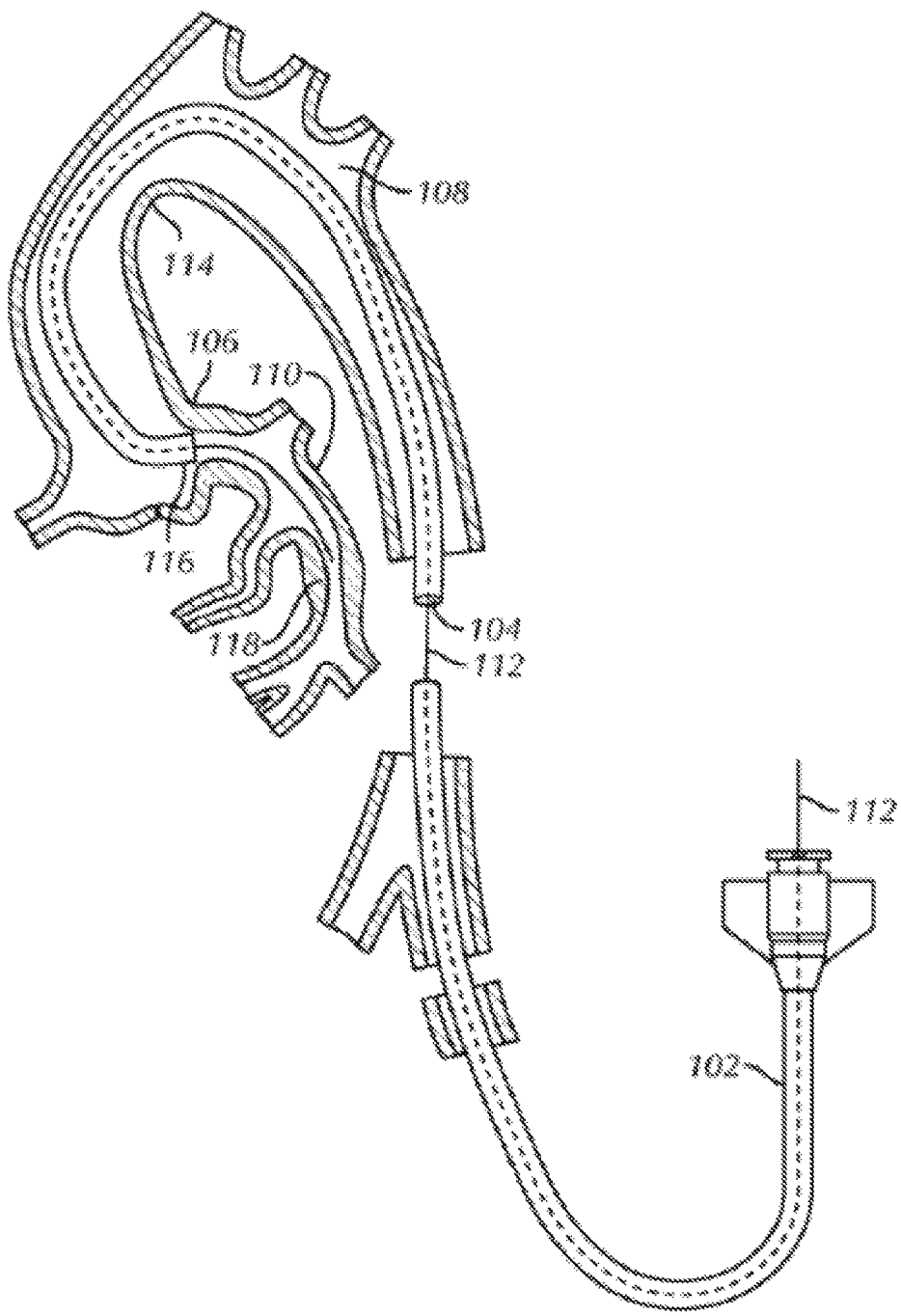
FIG. 1 illustrates a plan view of a guide catheter advanced through an aorta to an ostium of a coronary vessel.

Minimally invasive cardiac interventions are utilized throughout the world and often include the use of a guidewire 112 and a guide catheter 102, as illustrated in FIG. 1. The guidewire 112 can comprise an elongate, small-diameter member designed to navigate vessels to reach a diseased site or vessel segment of interest. Guidewires can come in various configurations, including solid steel or nitinol core wires and/or solid core wires wrapped in a smaller wire coil or braid, for example. The guide catheter 102 can comprise an elongate tube member defining a main lumen 104 along its length. The guide catheter 102 can be formed of polyurethane, for example, and can be shaped to facilitate its advancement to a coronary ostium 106 (or other region of interest within a patient's body). Any sized guide catheter 102, such as a 6F, 7F, 8F guide catheter, where F is an abbreviation for the French catheter scale (a unit to measure catheter diameter (1F=¼ mm)), can be inserted at a femoral or radial artery and advanced through an aorta 108 to a position adjacent to the ostium 106 of a coronary artery 110.

In a typical procedure, the guidewire 112 (or a shorter, thicker introducer guidewire) and the guide catheter 102 can be advanced through the arch 114 of the aorta 108 to the ostium 106. The guidewire 112 may then be advanced beyond the ostium 106 and into the coronary artery 110. The diameter and rigidity of the guide catheter's distal end 116, however, may not permit the device to be safely advanced beyond the ostium 106 and into the coronary artery 110.

Maintaining the position of the guide catheter's distal end 116 at the ostium 106 can facilitate the guidewire 112 or other interventional device successfully reaching the diseased site (e.g., a stenotic lesion 118) through its further distal advancement. With the guide catheter 102 in position, force can be applied to the guidewire's proximal end to push the guidewire 112 to and beyond the lesion 118, and a treating catheter (optionally including a balloon or stent) can be passed over the guidewire 112 to treat the site. The application of force to the guidewire 112 or the treating catheter can sometimes cause the guide catheter 102 to dislodge from the ostium 106 of the coronary artery 110, and, in such instances, the guidewire or treating catheter must be further distally advanced independently of the guide catheter's alignment and support to reach the lesion 118. This can occur in the case of a tough stenotic lesion 118 or tortuous anatomy, where it is often difficult to pass the guidewire 112 or the treating catheter to and beyond the lesion. A heart's intrinsic beat can also cause the guide catheter's distal end 116 to lose its positioning or otherwise be shifted so that it no longer is positioned to align and support the guidewire 112 or the treating catheter into the portion of the coronary artery 110 including the lesion 118.

Figure 2:
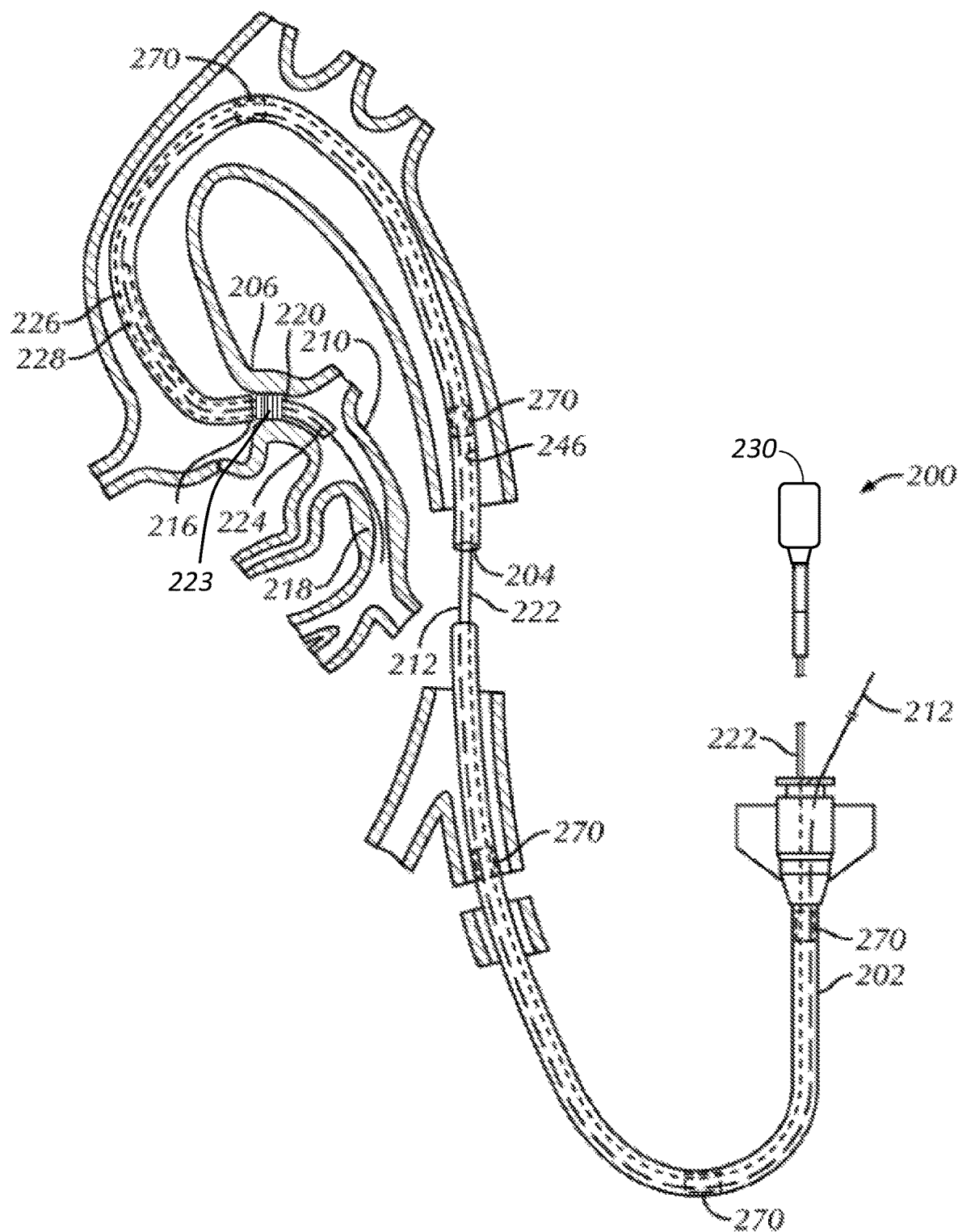
FIG. 2 illustrates a plan view of a guide extension catheter, as constructed in accordance with at least one embodiment, used in conjunction with a guide catheter for the delivery of an interventional device into an occluded vessel for treatment.

As illustrated in FIG. 2, the present guide extension catheter 200 can improve access to a coronary artery 210 and a stenotic lesion 218. The guide extension catheter 200 can include a relatively flexible elongate tube member 220 and a push member 222 having a collective length that is greater than a length of a guide catheter 202 (e.g., about 130 cm-about 175 cm, or greater). The elongate tube member 220 can be coupled to a balloon 223, such that the balloon 223 surrounds at least a distal portion of the tube member 220. An outer diameter of the tube member 220 can be sized to permit insertion of its distal end portion 224 into a coronary artery or its branches containing the lesion 218, thereby providing alignment and support for an interventional device (e.g., a treating catheter) beyond the distal end 216 of the guide catheter 202 to the lesion and beyond. The balloon 223 may have a variable outer diameter, which increases upon inflation and decreases upon deflation. In embodiments, an outer diameter of the balloon 223, when deflated, can be sized to permit insertion of the balloon 223 into a coronary artery or its branches containing the lesion 218, thereby augmenting the alignment and support for an interventional device provided by the distal end portion 224 of the tube member 220. After inflation, the balloon 223 may have an outer diameter approximately equal to, or slightly greater than, the cross-sectional inner diameter of a blood vessel, such that an outer surface of the balloon 223 contacts and applies a pressure to an inner surface of the blood vessel wall, further augmenting the alignment and support provided by the distal end portion 224 of the tube member 220. Optionally, a bioactive layer can be coated on an outer surface of the balloon for release into a wall of the blood vessel, thereby providing the vessel with augmented treatment. The bioactive layer can include one or more drugs, therapeutic agents, diagnostic agents, excipients, or combinations thereof, for example as described in commonly-owned U.S. Patent Application No. 62/719,000, which is incorporated by reference in its entirety herein.

In some embodiments, the diameter of the inflated balloon 223 can be increased or decreased along the longitudinal axis of the guide extension catheter 200, thereby providing additional locking capability for the balloon to the surrounding vessel and/or the guide catheter 202. For example, a proximal portion of the balloon 223 may have a larger diameter than a distal portion, such that the balloon applies greater force on the inner diameter of the guide catheter 202, which may be stronger than a blood vessel wall, thereby reducing the likelihood of vessel perforation or slippage of the guide extension catheter 200. In some embodiments, the distal portion of the balloon 223 may have a larger diameter than a proximal portion, for example if the target site within the vessel has a greater inner diameter than the guide catheter 202. The inflated balloon 223 may taper distally or proximally, or the inflated balloon 223 may define discrete, step-like portions of variable diameter. The extension of the tube member 220 surrounded by the balloon 223, especially when the balloon is inflated, into a smaller-sized artery or branch also serves to maintain the position of the guide catheter 202 at an artery's ostium 206 during an operation.

The operating physician can advance the distal end portion 224 of the tube member 220 over a guidewire 212 and through and beyond the guide catheter's distal end 216 into the coronary artery 210. A proximal end portion 226 of the tube member 220 can remain within the guide catheter 202. The physician can then inflate the balloon 223 using an external inflation device, e.g., inflation syringe, thereby securing the distal end portion 224 of the tube member within the coronary artery 210. The physician can subsequently deliver the treating catheter over the guidewire 212, through a main lumen 204 of the guide catheter 202, and through a lumen 228 of the tube member 220 until the working portion of the treating catheter is located beyond the distal end portion 224 of the tube member. The operating physician can then treat the lesion 218 using standard techniques with added back-up support on the guide catheter 202, thereby providing an extra ability to push and advance the treating catheter.

In general, the lumen 228, and hence the tube member 220, can be sized and shaped to pass one or more interventional devices such as the guidewire and the treating catheter therethrough. The cross-sectional shape of the lumen 228 can be similar to the cross-sectional shape of the guide catheter's main lumen 204. For instance, in some examples, the cross-sectional shape of the lumen 228 can be generally uniform along its length. In other examples, the cross-sectional diameter may vary along the length of the tube member 220. According to embodiments of such examples, the distal end portion 224 of the tube member 220 may be more narrow, e.g., tapered, relative to the proximal end portion 226, for instance. In addition or alternatively, the proximal and distal portions of the tube member 220 can be separated by one or more tapered portions. Various embodiments of the tube member 220 may include one or more tapered portions between and/or surrounding portions of the tube member 220 having a generally uniform diameter. The length of each differently-sized portion of the tube member 220 in such embodiments can also vary, and in some examples, the distal portion 224 of the tube member can be the longest. In examples that include differently sized proximal and distal portions, the difference in diameter between the proximal portion 226 and the distal portion 224 of the tube member may be from about 1F to about 4F, or anywhere in between.

The outer diameter of the balloon 223, when deflated, can assume maximum cross-sectional dimensions that allow the balloon 223, and the tube member 220 coupled radially therein, to coaxially slide into and through the guide catheter 202. In other embodiments, the outer cross-sectional dimensions of the deflated balloon 223 can be less than the allowable maximum. For example, in an 8F guide catheter, the deflated balloon 223 can have about a 7F, 6F, 5F, 4F or lesser diameter, or any diameter therebetween. In some embodiments, a diameter of the lumen 228 of the tube member 220, positioned within the balloon 223, is not more than about one French size smaller than a diameter of the lumen 204 of the guide catheter 202. In one embodiment, the guide extension catheter 200 can be made in at least three sizes corresponding to the internal capacity of about 8F, 7F, and 6F guide catheters that are commonly used in interventional cardiology procedures. The difference in size between the outer diameter of the deflated balloon 223 and the inner diameter of the guide catheter 202 may vary. For instance, the gap in cross-sectional diameter between the inner diameter of the guide catheter 202 and the outer diameter of the deflated balloon 223 may be less than and/or about 0.001 in., 0.002 in., 0.003 in., 0.004 in., or 0.005 in., or any distance therebetween. In specific embodiments, the cross-sectional diameter gap may range from about 0.002 to 0.003 in., or about 0.002 to 0.0035 in. The diameter gap may be substantially continuous along a substantial portion of the length or a majority of the length of the balloon 223 in some examples. The diameter gap between an outer diameter of the tube member 220 and the lumen 204 of the guide catheter 202 may also be generally continuous along a substantial portion of the length or a majority of the length of the tube member 220 in some embodiments, or the diameter gap may increase along one or more distal portions of the tube member 220. In various embodiments, a tube member 220 and balloon 223 with any diameter may be used, provided an outer surface of the tube member 220 contacts at least a portion of the inner surface of the balloon 223. The length of the tube member 220 can be substantially less than the length of the guide catheter 202; however, the tube member 220 can be designed with any length according to a desired application, such as about 6 to about 45 cm, about 10 to about 35 cm, about 14 to about 25 cm, or about 18 to about 20 cm.

The length of the balloon 223 in its coiled, i.e., not linear, operational configuration can also be substantially less than the length of the guide catheter 202, and in some examples, the length of the coiled balloon 223 may be equal or less than the length of the tube member 220. In embodiments, the length of the coiled balloon 223 may range from about 2 to about 45 cm, about 5 to about 35 cm, about 10 to about 25 cm, about 15 to about 22 cm, or about 18 to about 20 cm. In various examples, the length of the uncoiled, i.e., linear, balloon 223 may vary when creating a coil of a desired length based on the diameter of the inflatable tube(s) constituting the balloon 223. For example, the smaller the diameter of inflatable tube(s), the longer the length of the inflatable tube(s) necessary to create a coiled balloon 223 of a desired length. The position of the balloon 223 relative to the tube member 220 can also vary. For instance, the balloon 223 can be positioned a distance from the distal end of the tube member 220, as shown in the example of FIG. 2. In other examples, the balloon 223 can be positioned near a medial or distal portion of the tube member 220. In some embodiments, the position of the balloon 223 may depend on the cross-sectional diameter of the tube member 220. For instance, if the tube member 220 defines one or more tapered portions, the balloon 223 may be positioned so as not to overlap with such portions. A distal taper defined by the tube member 220 may allow it to access especially narrow and/or otherwise difficult-to-reach vessels or cavities, and positioning the balloon 223 proximal to such portions of the tube member 220 may situate the balloon for anchoring the tube member in the vessel without impeding its maximal extension therein. Once the tube member's distal end 224 reaches a targeted position, the balloon 223 can be inflated until its outer surface applies a radial force against an inner surface of the blood vessel and/or an inner surface of the guide catheter 202, such that the elongate tube member 220 is firmly secured at the site and the guide extension catheter 200 remains stationary.

The push member 222 can be attached to the proximal end portion 226 of the tube member 220 and can extend proximally from this attachment to a handle member 230 (also referred to as a manipulation member) accessible to an operating physician outside of a patient's body. The handle member 230 and the push member 222 can allow the physician to position the tube member 220 between a first position, entirely within the guide catheter 202, and the illustrated second position, in which the tube member's distal end 224 extends beyond that of the guide catheter 202 and into the coronary artery 210. As shown in FIG. 2, the balloon 223, or at least a distal portion thereof, may also be extended beyond the distal end of the guide catheter 202. The push member 222 can comprise a generally rigid portion that is rigid enough to allow the guide extension catheter 200 to be inserted through the guide catheter 202 upon receiving a pushing force from a physician via the handle member 230. The push member 222 can be more rigid along its longitudinal axis than the tube member 220, and may generally define a rail structure without a lumen through which interventional cardiology devices are insertable. In some examples, the push member 222 can have a maximal cross-sectional dimension at a proximal portion that is smaller than the cross-sectional outer diameter of the tubular flexible portion. Examples of the push member 222 can include one or more tubular or elongate structures, such as tubular bands 270, along its length to urge the member to one side of the guide catheter's inner wall surface 246, for example as described in U.S. patent application Ser. No. 15/581,176, which is incorporated by reference in its entirety herein.

Figure 3A:
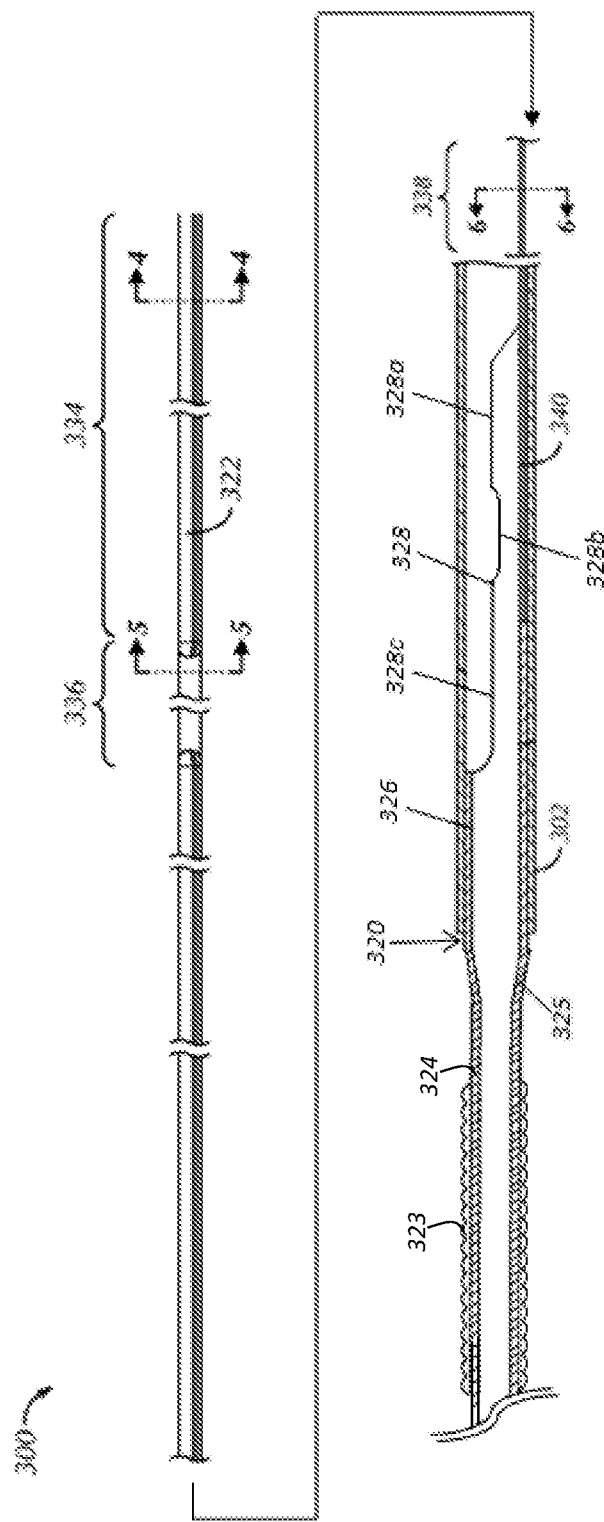
FIG. 3A illustrates a cross-sectional side view of a guide extension catheter, as constructed in accordance with at least one embodiment, partially within a sectioned guide catheter.
Figure 5:
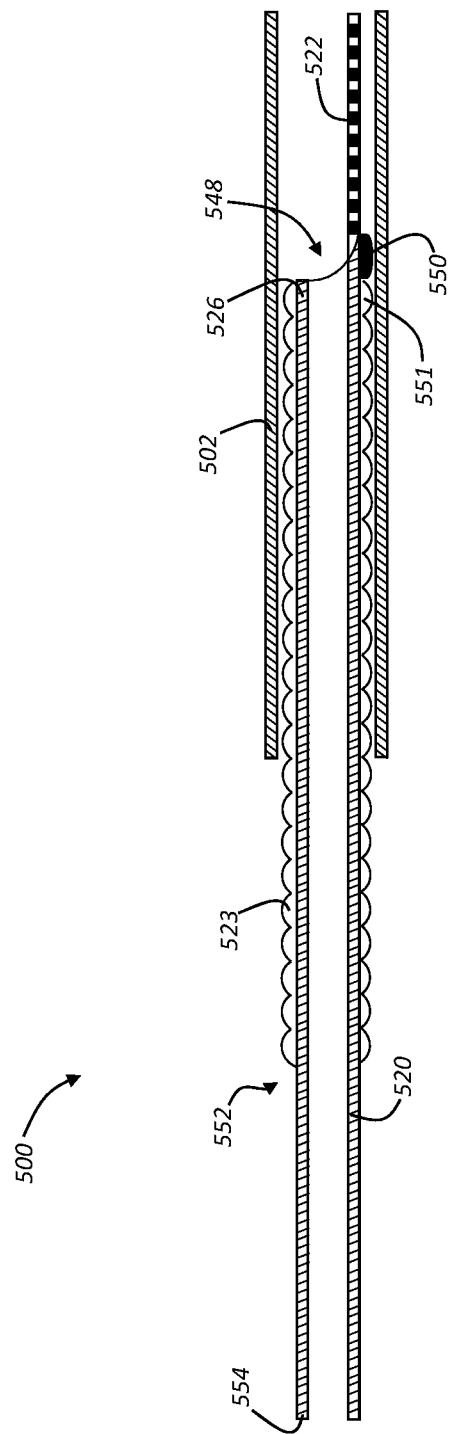
FIG. 5 illustrates a cross-sectional side view of a guide extension catheter, as constructed in accordance with at least one embodiment, partially within a sectioned guide catheter.

FIG. 3A illustrates a cross-sectional side view of an example guide extension catheter 300 partially positioned within a guide catheter 302. This side view illustrates in greater detail the components of the extension catheter 300 according to one embodiment, including an inflatable balloon 323 surrounding a portion of a relatively flexible elongate tube member 320. FIG. 3A also shows a push member 322, which can be rigid enough to urge the tube member 320 through the vasculature in response to receiving an axial force applied at a proximal end thereof, e.g., by a physician. The embodiment shown also includes distinct portions of the tube member 320 defined by different diameters. As shown, the tube member 320 can define a narrow distal portion 324, a tapered middle portion 325, and a wider proximal portion 326. In additional embodiments, the tube member 320 may not be tapered, and may instead define a constant or generally constant diameter along its length, for example as shown in FIG. 5.

The stiffness of the push member 322 may be generally uniform, or substantially uniform, along its length. In certain examples, the push member 322 can include a plurality of segments or portions having different stiffness and flexibility profiles to provide the guide extension catheter 300 with a desired combination of pushing force and vessel placement capabilities. In one embodiment of such examples, the push member 322 can include three segments 334, 336, 338 having different stiffness and flexibility profiles: relative high stiffness and low flexibility at a proximal end portion 334 of the push member, relative medium stiffness and flexibility in an intermediate portion 336 of the push member, and relative low stiffness and high flexibility at a distal end portion 338 of the push member. In some embodiments, the length of the first segment 334 can constitute between 50% and 90% of the entire length of the guide extension catheter 300, the length of the third segment 338 can constitute between 2% and 10% of the catheter's length, and the remaining length can be attributed to the second segment 336. More or less segments of differing stiffness and flexibility profiles can also be used and accomplished through variation of one or more materials, geometric shapes or geometrical sizes of the push member 322. The length of each segment may also vary.

In some embodiments, the push member 322 can be an elongated solid wire of generally constant or varying dimensions and can be made of a polymeric or metallic material, such as high tensile stainless steel (e.g., 304V, 304L or 316LV), mild steel, nickel-titanium allows, nickel-chromium-molybdenum alloys, nickel-copper alloys, nickel-tungsten alloys or tungsten alloys. The push member 322 can be coated with a hydrophilic, silicone or other friction-reducing material. In some examples, the push member 322 may comprise a hypotube defined by a generally circular or oval-shaped cross-section, or any other desired configuration.

Figure 3B:
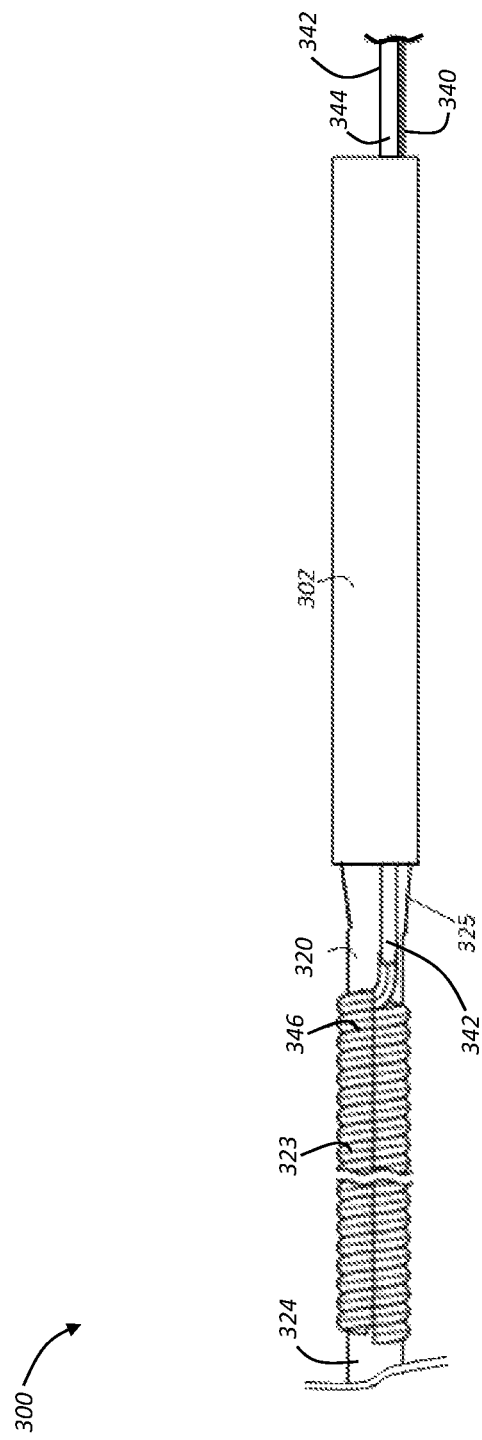
FIG. 3B illustrates a side view of the guide extension catheter of FIG. 3A, as constructed in accordance with at least one embodiment, partially within a guide catheter.

The balloon 323 can be formed of an inflatable tube coupled with an elongate shaft having a lumen for providing inflation fluid to, or withdrawing inflation fluid from, the balloon, as further shown in FIG. 3B. The inflatable tube can be coiled in a helical manner around a central axis into a series of windings, for example as described in U.S. patent application Ser. Nos. 14/850,095 and 15/296,183, which are incorporated by reference in their entireties herein. Adjacent windings can be stacked against and bonded to each other, and an inner surface of the series of windings can contact an outer surface of the tube member 320. Alternatively, adjacent windings may be spaced apart such that they do not contact each other. Spaced windings may be preferred for non-coronary applications, which may involve positioning the balloon in vessels of greater diameter. The inner surface of the windings can be coupled with the outer surface of the tube member 320 in various ways. For example, the balloon 323 can be heat-treated until the balloon adheres to the tube member 320. In some examples, an outer surface of the elongate tube member 320 can be inset in the inner surfaces of the windings constituting the balloon 323. An adhesive deposited between the tube member and the balloon may also be used to couple the two components. In the example shown in FIG. 3A, the balloon 323 is coupled with a distal portion 324 of the tube member 320. In other examples, the balloon 323 may be coupled with a proximal portion 326 of the tube member 320 instead of or in addition to the distal portion 324.

In some examples, the tube member 320 can be formed from an inner polymer layer, an outer polymer layer, and/or a reinforcement member (e.g., braid or coil) disposed between or adjacent to the polymer layers. According to such examples, the inner polymer layer can be composed of, or coated with, silicone, polytetrafluoroethylene (PTFE) or another lubricious material to provide a slippery surface for received interventional devices. The outer polymer layer can include one or more flexible materials, such as polyurethane, polyethylene or polyolefin of sequentially diminishing durometers along the tube member's length, and it can be coated with a friction-reducing material (e.g., a hydrophilic material) to facilitate insertion and trackability through vasculature and a guide catheter. The reinforcing braid or coil, in embodiments featuring a braid or coil, can be formed of stainless steel or a platinum alloy, for example, and can extend between the polymer layers along at least a portion of the tube member's length.

Figure 11A:
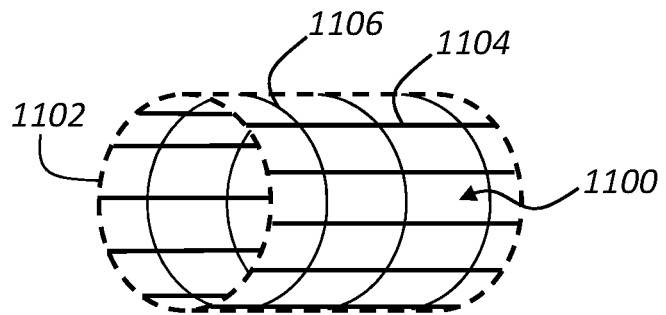
FIG. 11A illustrates a perspective view of a reinforcement member included in a guide extension catheter in accordance with at least one embodiment.
Figure 11B:
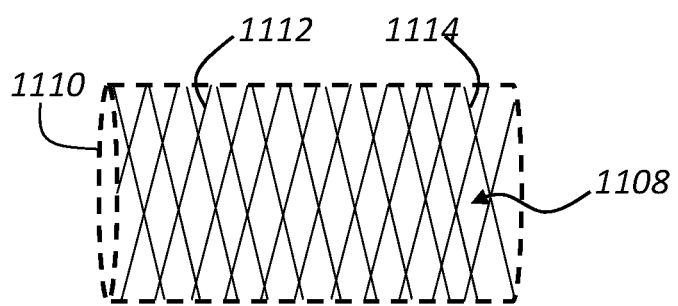
FIG. 11B illustrates a perspective view of another reinforcement member included in a guide extension catheter in accordance with at least one embodiment.

The optional reinforcement member disposed between the polymer layers of some elongate tube members 320 can be configured in multiple ways. For instance, the reinforcement member may lack a braid, coil or other distinct reinforcing structure, and may instead comprise one or more materials having greater stiffness than the remaining portions of the tube member 320. In addition or alternatively, embodiments of the reinforcement member can include different reinforcing structures, e.g., a generally rigid sleeve, elongate member, and/or bars or strips of rigid or semi-rigid material, as shown in FIGS. 11A and 11B. Additional components and/or materials configured to increase the rigidity of a portion of the tube member 320 are also contemplated. At least in part because the components of the reinforcement member may vary, methods of assembling the reinforcement member may also vary. For example, if the reinforcement member disposed between the polymer layers of the elongate member 320 includes a coil, various types of coils may be used, and in some examples, each coil can be coupled with other components of the tube member 320 in a distinct manner, which may depend on whether the cross-sectional diameter of the tube member is generally uniform or varied. In embodiments, if the size of the coil matches the smaller distal portion 324 of the tube member 320, the coil can be first loaded over the distal portion 324. If the size of the coil is larger, such that it approximately matches the larger diameter of the proximal portion 326, the coil can be first loaded onto the proximal portion 326.

The proximal end portion 326 of the tube member 320 can be eccentrically coupled to a distal end portion 340 of the push member 322 at its periphery or circumference and can provide a generally smooth transition between the members in some examples. The arrangement or configuration of this coupling can vary. For example, embodiments may include a funnel or a protective lip member, e.g., comprised of nitinol, positioned between the distal end portion 340 of the push member 322 and the proximal portion 326 of the tube member 320 to prevent the push member 322 from contacting the balloon 323.

In some embodiments, the tube member 320 can include a side opening formed at a proximal end of its peripheral wall. The configuration of the side opening may also vary. For example, the side opening may be approximately perpendicular to the longitudinal axis of the push member 322, or the side opening may be sloped or slanted such that the transition between the push member 322 and the full circumferential portion of the tube member 320 is relatively gradual. In some examples, the push member 322 can be disposed within the opening. Inserting the push member 322 into the opening can result in a mechanical coupling between the members and additional or alternative bonds (e.g., adhesive bonds, thermal bonds, welds, brazes, etc.) can be utilized. The distal end portion 340 of the push member 322 can be flattened in some embodiments to provide a larger surface area to secure to the tube member 320. In addition or alternatively, coupling mechanisms facilitated by a third component 332 (e.g., a metal or polymer skived (slanted) collar or concave track) bonded between or integrated with the proximal end portion 326 of the tube member 320 or the distal end portion 340 of the push member 322 are also contemplated. Metallic or polymeric structures forming the third component 332 can become less stiff and more flexible in a proximal-to-distal direction, for instance, to provide a gradual flexibility transition between the more rigid push member 322 and the more flexible tube member 320.

In embodiments featuring a concave track 328, such as the example shown in FIG. 3A, the degree of enclosure defined by the concave track 328 can vary along its length. In one embodiment, a first segment 328a of the concave track 328 can define an approximately 200° enclosure, a second segment 328b of the concave track can define an approximately 170° enclosure, and a third segment 328c, closer to the tube member 320, can define an approximately 200° enclosure, which transitions to 360° just before reaching the most proximal end of the tube member's proximal portion 326. Accordingly, the concave track 328 may transition, proximally to distally, from more enclosed to less enclosed, and back to more enclosed before reaching the proximal end portion 326 of the tube member 320. The specific degree of enclosure defined by each portion of the concave track 328 may vary, along with the number of distinct portions constituting the concave track 328. For example, the degree of enclosure defined by each portion may be increased or decreased by up to 5°, 10°, 15°, 20°, 25°, 30°, 40°, 50°, 60°, or more. In operation, the intermediary valley of the concave track 328, i.e., the second segment 328b, along with the embedded push member 322, may be urged to one side of the guide catheter's inner wall surface such that the track 328 and push member 322 may be concentrically aligned within guide catheter 302, thereby providing a clear path through the guide catheter and into the tube member 320 for a guidewire and a treating catheter. This clear path can eliminate twisting and prevent a guidewire, e.g., guidewire 212, from becoming entangled with, e.g., wrapped around, the push member 322 during use of the guide extension catheter 300. Alleviation of twisting may be especially apparent in operations requiring multiple, simultaneously inserted guidewires.

In some embodiments, the concave track 328 can define a partially cylindrical opening, e.g., resembling a half-pipe, and having a length of about 1 cm to about 4 cm, 8 cm, 12 cm, 16 cm, 18 cm, 20 cm, 22 cm, 24 cm, 26 cm, or more, or any length therebetween. In one example, the concave track 328 may be about 17 cm long. In various embodiments, the length of each discernible portion 328a, 328b, 328c of the concave track 328 may range from about 1 cm, 2 cm, 4 cm, 6 cm, 8 cm, 10 cm, or 12 cm, or any length therebetween. The length of each portion 328a, 328b, 328c may be the same or different. In some examples, the concave track 328 may include less than three distinct portions. For example, the concave track 328 may define an elongated tapered portion. The concave track 328 can be accessible from a longitudinal side defined transverse to a longitudinal axis of the tube member 320 and can provide a larger area to receive an interventional device into the tube member than an area associated with an opening oriented perpendicular to the longitudinal axis of the tube member 320. Optionally, the concave track 328 can be sized larger than the proximal end portion 326 of the tube member 320 to more effectively align and funnel a treating catheter across the coupling transition and into the tube member 320. This larger size of the concave track 328 can be accomplished by incorporating a nickel-titanium alloy, for example, which can expand post-implant to a size of the guide catheter's inner wall surface.

Markers on the push member 322, the tube member 320, and/or the balloon 323 can allow an operating physician to identify positioning of the guide extension catheter's components relative to patient anatomy, the guide catheter 302, and any interventional devices used during a procedure. For example, one or more depth markers can be printed on an outer surface of the push member 322 and can be positioned at predetermined lengths relative to a distal end of the tube member 320. One or more radiopaque marker bands can be positioned on the tube member 320. The marker bands can be composed of tungsten, platinum or an alloy thereof and can have a metallic band structure. Alternatively, for space conservation reasons, the marker bands can be formed by impregnating portions of the tube member 320 with a radiopaque filler material, such as barium sulfate, bismuth trioxide, bismuth carbonate, powdered tungsten, powdered tantalum or the like. A first marker band can be positioned slightly distal to a fully-round entrance of the tube member 320 and a second marker band can be positioned near the tube member's distal end, for example.

Methods of manufacturing the guide extension catheters described herein may involve stretching an inner PTFE lining of the elongate tube member 320. In embodiments featuring a tapered elongate tube member 320, the PTFE lining may require excess stretching relative to comparable, but non-tapered tube members, and the outer surface of the lining can be etched to maintain the desired polymer chemistry of the PTFE, thereby ensuring adhesion between the fluoropolymers of the lining and an outer polymer layer (e.g., PEBAX) wrapping.

FIG. 3B shows a side view of the guide extension catheter 300 of FIG. 3A, as constructed in accordance with at least one embodiment, partially within a guide catheter. As shown, the guide extension catheter 300 can include an elongate shaft 342, which includes a lumen 344 for providing inflation fluid to, or withdrawing inflation fluid from, the balloon 323. The elongate shaft 342 can be eccentrically attached to a proximal portion 346 of the balloon 323 and can extend proximally for clinician accessibility outside the guide catheter. The lumen 344 of the elongate shaft 342 can be in fluid communication with the interior of the inflatable tube. In some examples, the elongate shaft 342 can be attached to the balloon 323 by wrapping the balloon 323 about a portion of the shaft and affixing it thereto. The elongate shaft 342 may extend in a proximal direction toward an external inflation device, extending adjacent to the push member 322, a proximal portion 340 of which is shown in FIG. 3B. The elongate shaft 342 can extend a length of about 100 cm to about 180 cm and can possess the qualities of compression rigidity along its longitudinal axis, which facilitates advancement of the balloon 323 through a patient's vascular system, and a distal flexibility sufficient to allow maneuverability through directional changes in the vascular system and prevent damage to the vessel during insertion. Portions of the elongate shaft 342 can include a PTFE coating to facilitate its advancement through the patient's vascular system. As shown in FIGS. 6B-8B, embodiments may also lack a separate elongate shaft. According to such embodiments, an inflation lumen may be defined within the push member, which may be coupled to the balloon.

The inflatable tube of the balloon 323 can include two different polymer tubes, one slightly smaller than the other. The smaller, inner tube can be formed from a polymer having sufficient radial stiffness to resist collapse or bursting when exposed to inflation pressures, and the larger, outer tube can be formed from a polymer configured to exhibit adhesive properties when heated. The balloon 323 can include any number of windings in a number of sizes and configurations depending upon the particular size and configuration of the tube member, the dimensions of the treatment site, the type of procedure being performed and/or the patient. Increasing the number of windings in the balloon 323 can increase the back-up support provided by the guide extension catheter.

Once at the treatment site, the balloon 323 can be inflated, as shown in FIG. 3B. Fluid under pressure can be supplied to the balloon 323 through the inflation lumen 344 of the elongate shaft 342, thereby expanding the balloon 323 toward a wall of a blood vessel. When inflated, the balloon 323 can impinge upon or engage the vessel wall at the treatment site, or at a location proximal to the treatment site, e.g., ostium proximal to a distal vessel site, at pressures of less than about 2 atm, greater than about 20 atm, about 2 atm to about 20 atm, about 4 atm to about 18 atm, about 6 atm to about 16 atm, about 8 atm to about 14 atm, about 10 atm to about 14 atm, or any pressure therebetween, for example. The outward radial pressure exerted by the balloon 323 against the vessel wall can secure the guide extension catheter 300 firmly in place without puncturing the vessel wall, even amidst backward force that may be experienced during an operation. In some embodiments, the balloon 323 can be inflated at least partially within the guide catheter 302, impinging upon its inner surface at similar pressures. When the procedure is completed, the balloon 323 can be deflated by applying a vacuum to a proximal manifold coupled with the inflation lumen 344 of the elongate shaft 342.

Figure 4:
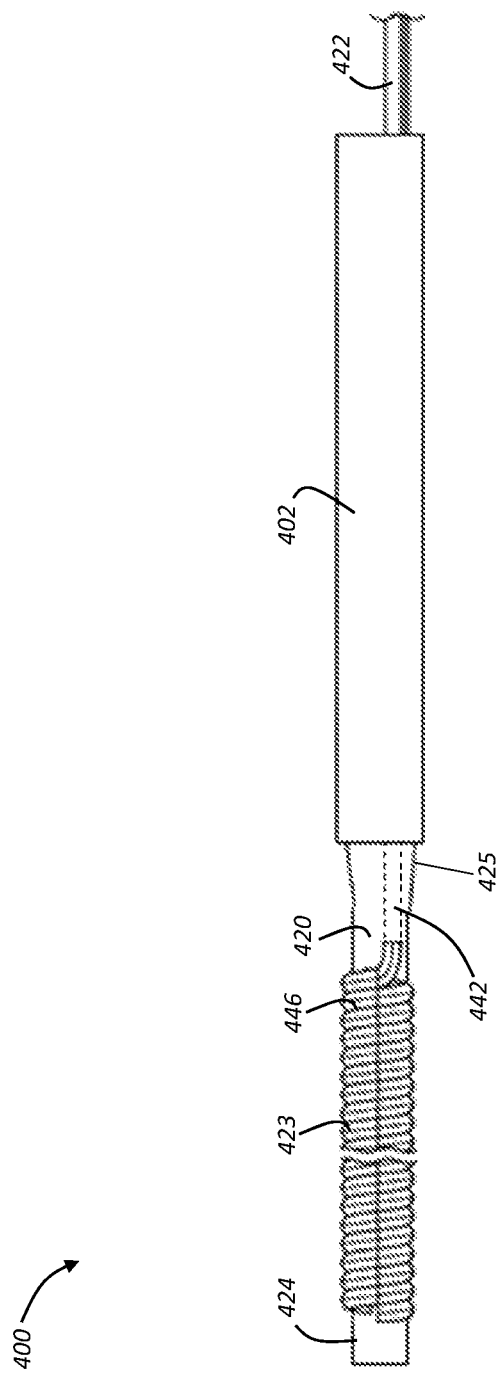
FIG. 4 illustrates a side view of a guide extension catheter, as constructed in accordance with at least one embodiment, partially within a guide catheter.

FIG. 4 illustrates a side view of a distal portion of a guide extension catheter 400, as constructed in accordance with at least one embodiment, partially within a guide catheter 402. An inflatable balloon 423 surrounds a distal portion 424 of an elongate tube member 420, which includes a tapered portion 425 in this example. A push member 422 is also coupled with the elongate tube member 420. As further shown, the elongate tube member 420 may include an integrally formed, internal elongate shaft 442 configured to provide inflation fluid to, and withdraw inflation fluid from, the inflatable balloon 423. The internal elongate shaft 442 may extend through the push member 422, to an external inflation device.

FIG. 5 illustrates a cross-sectional side view of a distal portion of a guide extension catheter 500, a portion of which is shown protruding from a guide catheter 502. The guide extension catheter 500 includes an elongate tube member 520 coupled at a proximal end 526 to a push member 522 and surrounded by a balloon 523. The elongate tube member 520 includes a proximal side opening 548, which in this example, features a sloped surface transitioning gradually toward the push member 522. To prevent the push member 522 from impacting the proximal end 551 of the balloon 523, a lip member 550 is also included at the proximal end 526 of the tube member 520.

As further shown in FIG. 5, the tube member 520 may have a generally constant diameter. The balloon 523 can extend various lengths along the tube member 520. In the example shown, the balloon 523 extends from the proximal end 526 of the tube member 520 to an approximately medial portion 552 of the tube member 520. In additional embodiments, the balloon 523 may extend greater or lesser distances along the length of the tube member 520. For example, the balloon 523 may extend from the proximal end 526 of the tube member 520 to the tube member's distal tip 554.

Figure 6A:
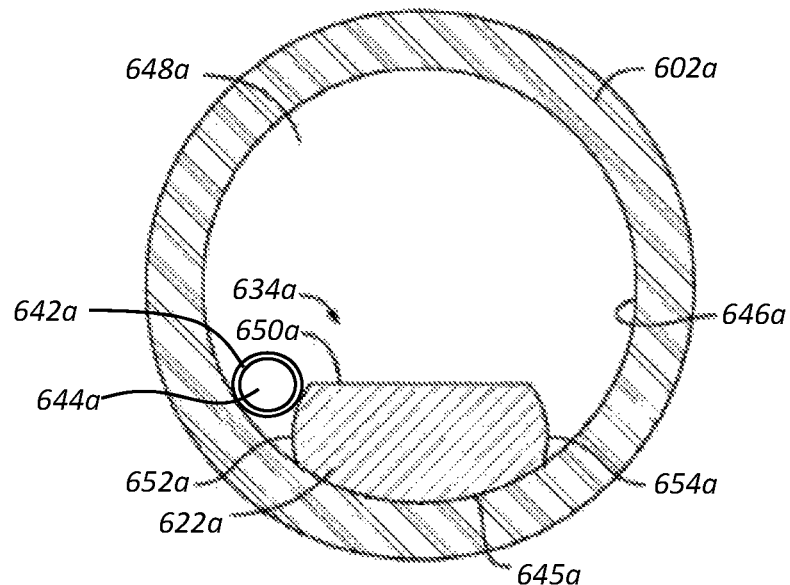
FIG. 6A illustrates a cross-sectional view along the length of a guide extension catheter, as constructed in accordance with at least one embodiment, within a guide catheter, where a lumen is positioned at a periphery of a push member.

FIGS. 6A-8B illustrate that an inflation lumen connecting an inflation device to a distal balloon may be provided in any desired manner. In some embodiments, the inflation lumen may be provided within the pushrod of the guide extension catheter. In other embodiments, the inflation lumen may be provided on a periphery of the guide extension catheter's pushrod, either as a separate, optionally attached structure, or integral with the pushrod. For example, FIG. 6A illustrates a cross-sectional view of a proximal end portion 634a of an example lumen-less push member 622a and an example of an elongate shaft 642a, such as along line 4-4 of FIG. 3A, within a guide catheter 602a. The cross-sectional shape and dimensions of the push member 622a and the elongate shaft 642a may vary. For example, embodiments of the push member 622a may include a lumen, but the lumen may be sized or positioned in a manner insufficient for inflating a distal balloon. The elongate shaft 642a can define a lumen 644a for delivering inflation fluid to, or withdrawing inflation fluid from, a distal balloon. The elongate shaft 642a can include a stainless steel hypotube, and some embodiments may also include a support wire configured to transmit forces applied by a treating clinician to either advance or retract the balloon during a treatment procedure. While lumen 644a is depicted as round, any desired configuration may be used. For example, the lumen could be square, polygonal, an irregular shape, or any other desired configuration. Further, while the elongate shaft 642a is depicted as a circular shaft proximate push member 622a, it could be any desired configuration and it could share a sidewall or surface with push member 622a. Elongate shaft 642a may be a separate structure from but proximate to push member 622a, and elongate shaft 642a may be but need not be affixed in whole or in part to push member 622a. In certain embodiments, elongate shaft 642a and push member 622a could be an integral unit.

Figure 6B:
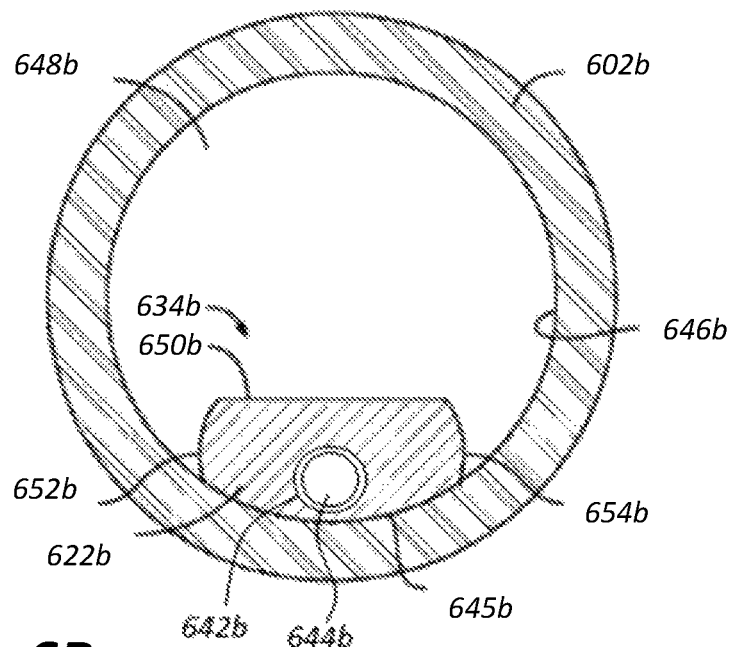
FIG. 6B illustrates an alternative embodiment of the cross-sectional view of FIG. 6A, where a lumen is positioned in an interior of a push member.

As shown in FIG. 6B, in some embodiments elongate shaft 642b may be provided with a lumen 644b that passes through, or is defined by, push member 622b. According to such examples, the push member 622b may be coupled, at a distal end, to a proximal end of an inflatable balloon. The shape of the elongate shaft 642b may vary, along with the shape of the push member 622b. FIG. 6B depicts lumen 644b with a circular cross section, but any desired geometry, including rectangular, irregular, oval, oblong, and/or cross-sectional shapes, are also within the scope of this disclosure. Further, FIG. 6B depicts lumen 644b generally centered within push member 622b, but lumen 644b may be located at any desired position within push member 622b, including at or on a periphery of push member 622b.

As further shown in the embodiments of both FIGS. 6A and 6B, the outer cross-sectional shape of the push member 622a/b can be defined by an arcuate first surface 645a/b configured to engage an inner wall surface 646a/b of the guide catheter 602a/b. The arcuate or curved shape of the first surface 645a/b can follow the inner wall surface 646a/b of the guide catheter 602a/b, providing smooth relative movements between the guide extension catheter and the guide catheter. The arcuate shape of the first surface 645a/b can also help to maximize axial or column strength of the push member 622a/b for force transfer from an operating physician to the rest of the guide extension catheter without reducing the effective delivery area 648a/b within the guide catheter 602a/b through which an interventional device can be advanced, for example as described in U.S. patent application Ser. No. 15/581,176, which is incorporated by reference in its entirety herein.

A second surface 650a/b of the proximal end portion's cross-section, which can be positioned opposite the first surface 645a/b, can be flat, substantially flat, concave, convex, curved, or any other desired configuration.

The cross-section at the proximal end portion of the push member 622a/b can be further defined by third and fourth surfaces 652a/b, 654a/b, which may also be arcuate, linear, curved, or any other desired configuration, that connect the first and second surfaces 645a/b, 650a/b. The cross-sectional shape and dimensions of push member 622a and 622b may be generally the same, or they may vary.

The guide extension catheters disclosed herein can include one or more push members of various configurations. For instance, additional embodiments of the push member 622a/b may lack one or more features illustrated in FIGS. 6A and 6B. The push member 622a/b may not define, for example, an arcuate first surface 645a/b and/or an arcuate third or fourth surface 652a/b, 654a/b. Such embodiments may feature one or more generally straight or concave surfaces of varying cross-sectional dimensions. In some examples, the push member 622b may lack the elongate shaft 642b, but may still define the lumen 644b to preserve the material properties of the push member 622b, such that a push member defining the lumen 644b may have the same or similar flexibility along its length as a push member lacking a lumen.

Figure 7A:
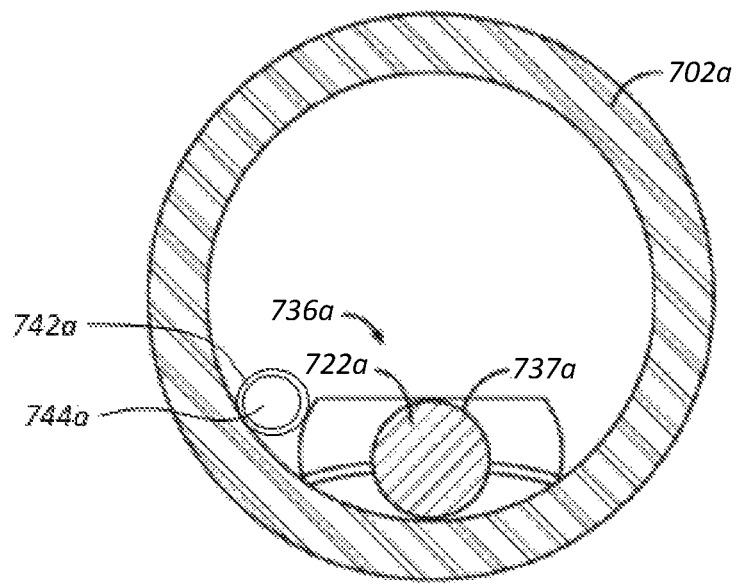
FIG. 7A illustrates a cross-sectional view along the length of a guide extension catheter, as constructed in accordance with an alternative embodiment of the guide extension catheter, within a guide catheter, where a lumen is positioned at a periphery of a push member.

FIG. 7A illustrates a cross-sectional view of an intermediate portion 736a of an example lumen-less push member 722a, such as along line 5-5 of FIG. 3A, within a guide catheter 702a. As shown, the intermediate portion 736a can be circular or oval in cross-section and defined by a circumferential surface 737a, which can reduce the tendency for a guidewire to become engaged with the push member 722a during use. In other embodiments, other geometries and/or configurations may be provided. Elongate shaft 742a may be adjacent to the push member 722a, defining a central lumen 744a for providing inflation fluid to a distal balloon. While lumen 744a is depicted as round, any desired configuration may be used. For example, the lumen could be square, polygonal, an irregular shape, or any other desired configuration. Further, while the elongate shaft 742a is depicted as a circular shaft proximate intermediate portion 736a, it could be any desired configuration and it could share a sidewall or surface with intermediate portion 736a. Elongate shaft 742a may be a separate structure from but proximate to intermediate portion 736a, and elongate shaft 742a may be but need not be affixed in whole or in part to intermediate portion 736a. In certain embodiments, elongate shaft 642a and intermediate portion 736a could be an integral unit.

Figure 7B:
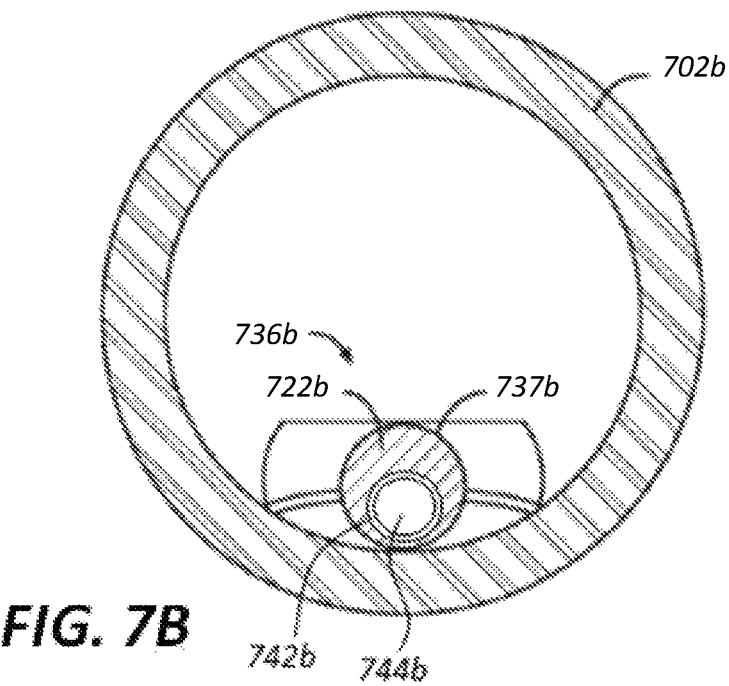
FIG. 7B illustrates the cross-sectional view of FIG. 7A, where a lumen is positioned in an interior of a push member.

As shown in FIG. 7B, in some embodiments elongate shaft 742b may be provided with a lumen 744b within a push member 722b, which may be otherwise dimensioned similarly or identically to push member 722a. Examples may lack elongate shafts 742a/b, but still include an internally defined lumen 744b. Further, FIG. 7B depicts lumen 744b with a circular cross section, but any desired geometry, including rectangular, irregular, oval, oblong, and/or cross-sectional shapes, are also within the scope of this disclosure. Further, FIG. 7B depicts lumen 744b generally centered within push member 722b, but lumen 744b may be located at any desired position within intermediate portion 736a, including at or on a periphery of push member 722b and/or intermediate portion 736a.

In some embodiments, the intermediate portions 736a/b of push member 722a and/or 722b can be rectangular in cross-section and defined by first, second, third and fourth flat surfaces, or can be bread loaf in cross-section and defined by three arcuate surfaces and one flat surface like the proximal end portion. In these alternative embodiments, a distance change between center points of the first and second surfaces at the push member's proximal end portion (FIG. 6A/B) to center points of the first and second surfaces at the push member's intermediate portion may be less than a distance change between center points of the third and fourth surfaces at the push member's proximal end portion to center points of the third and fourth surfaces at the push member's intermediate portion.

As yet another alternative, the intermediate portion 736a/b can have a cross-section defined by arcuate first and second surfaces. An arcuate first surface can have the same or substantially the same radius of curvature as the guide catheter's inner wall surface. An arcuate second surface can extend from a first end of the first surface to a second end of the first surface. Regardless of shape, the cross-section of the intermediate portion 736a/b of the push member can define an area less than an area of the cross-section of the proximal end portion (FIG. 6A/B) of the push member 722a/b in some examples.

Figure 8A:
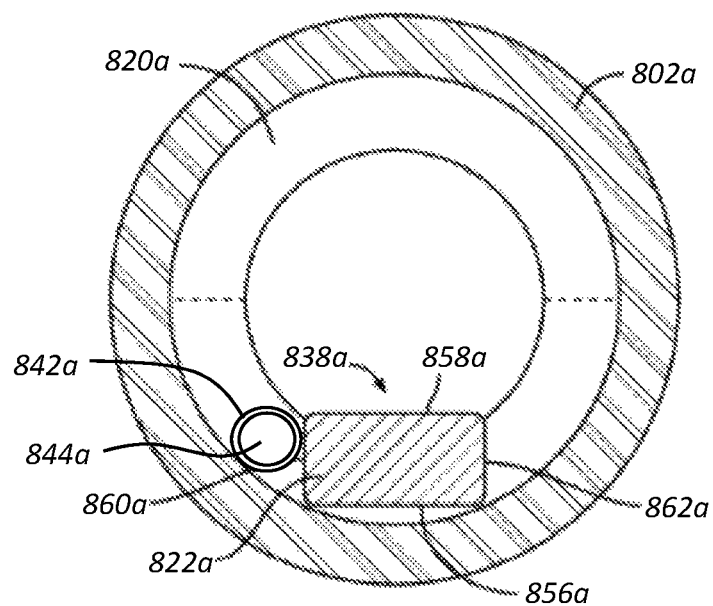
FIG. 8A illustrates a cross-sectional view along the length of a guide extension catheter, as constructed in accordance with another alternative embodiment of the guide extension catheter, within a guide catheter, where a lumen is positioned at a periphery of a push member.

FIG. 8A illustrates a cross-sectional view of a distal end portion 838a of an example lumen-less push member 822a, such as along line 6-6 of FIG. 3A, within a guide catheter 802a. The distal end portion 838a can be generally rectangular in cross-section and defined by first, second, third and fourth surfaces 856a, 858a, 860a, 862a, which may be flat, substantially flat, or curved, or a combination of these. The cross-section of the distal end portion 838a can define an area less than an area of the cross-section of the proximal end (FIG. 6A/B) and intermediate (FIG. 7A/B) portions of the push member 822a in some examples. The cross-section of the proximal end portion can gradually transition along the length of the push member 822a to the distal end portion 838a, which can couple to a tube member 820a. The distal end portion 838a can define a flattened rectangular cross-section in some examples, or alternatively can define a bread loaf cross-sectional shape defined by three arcuate surfaces and one flat or substantially flat surface. Additional cross-sectional shapes and dimensions of the distal end portion 838a are also contemplated, and the guide extension catheters disclosed herein are not limited to one or more configurations of the push member 822a.

As further shown, the separate elongate shaft 842a defining a lumen 844a may run adjacent to the push member 822a. A means to affix an outer surface of the elongate shaft 842a and the flexible material of the balloon can be employed to withstand stresses associated with pressure changes and inflation and deflation of the balloon. It can be important that the affixing means create a fluid tight seal between the two materials and restrict any delamination along the seal line during periods of working pressures. In some embodiments, the elongate shaft 842a coupled with the balloon can be covered with nylon as part of the affixing means. The materials can be joined by an adhesive process, such as cyanoacrylate, epoxy or urethane compounds, or joined by a heat treatment or pressure fit process that melts or welds the two materials together. In another embodiment, elongate shaft 842a is integral with push member 822a.

While lumen 844a is depicted as round, any desired configuration may be used. For example, the lumen could be square, polygonal, an irregular shape, or any other desired configuration. Further, while the elongate shaft 842a is depicted as a circular shaft proximate push member 822a, it could be any desired configuration and it could share a sidewall or surface with push member 822a. Elongate shaft 842a may be a separate structure from but proximate to push member 822a, and elongate shaft 842a may be but need not be affixed in whole or in part to push member 822a. In certain embodiments, elongate shaft 842a and push member 822a could be an integral unit.

Figure 8B:
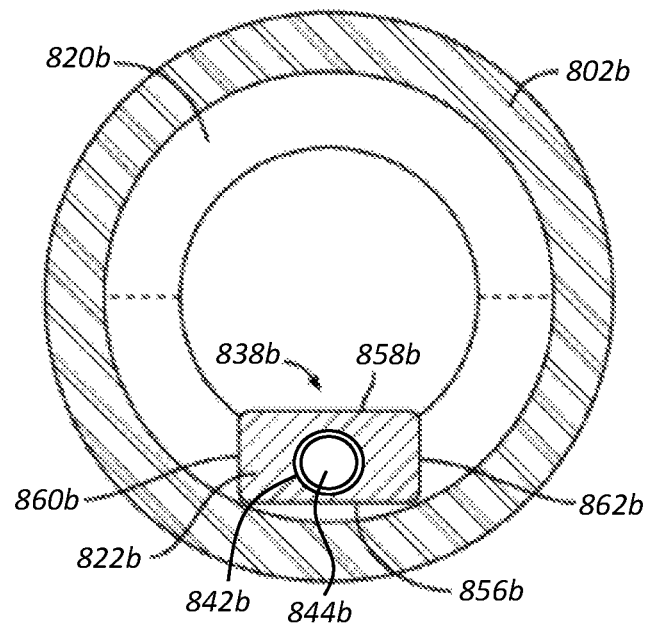
FIG. 8B illustrates the cross-sectional view of FIG. 8A, where a lumen is positioned in an interior of a push member.

FIG. 8B illustrates an embodiment where lumen 844b is provided within push member 822b, which may be otherwise similar or identical to lumen-less push member 822a. In some examples, the push member 822b may lack shaft 842b, defining an internal lumen 844b, only. Further, FIG. 8B depicts lumen 844b with a circular cross section, but any desired geometry, including rectangular, irregular, oval, oblong, and/or cross-sectional shapes, are within the scope of this disclosure. Further, FIG. 8B depicts lumen 844b generally centered within push member 822b, but lumen 844b may be located at any desired position within push member 822b, including at or on a periphery of push member 822b.

FIGS. 6A-8B illustrate that the push member 622a/b, 722a/b, 822a/b of a guide extension catheter can be designed to be sufficiently small, taking up relatively little space within the lumen of a guide catheter, while still being sufficiently sized and configured for exceptional pushability and kink resistance when advancing the extension catheter during an interventional procedure. Accordingly, use of the present guide extension catheters allows for an interventional device to be advanced through and beyond the guide catheter to reach a desired distal target location for intervention. FIGS. 6A-8B also demonstrate that an elongate shaft defining a lumen for delivering inflation fluid to, and withdrawing fluid from, an inflatable balloon can be included separately from, or integrally within, the push member.

Figure 9:
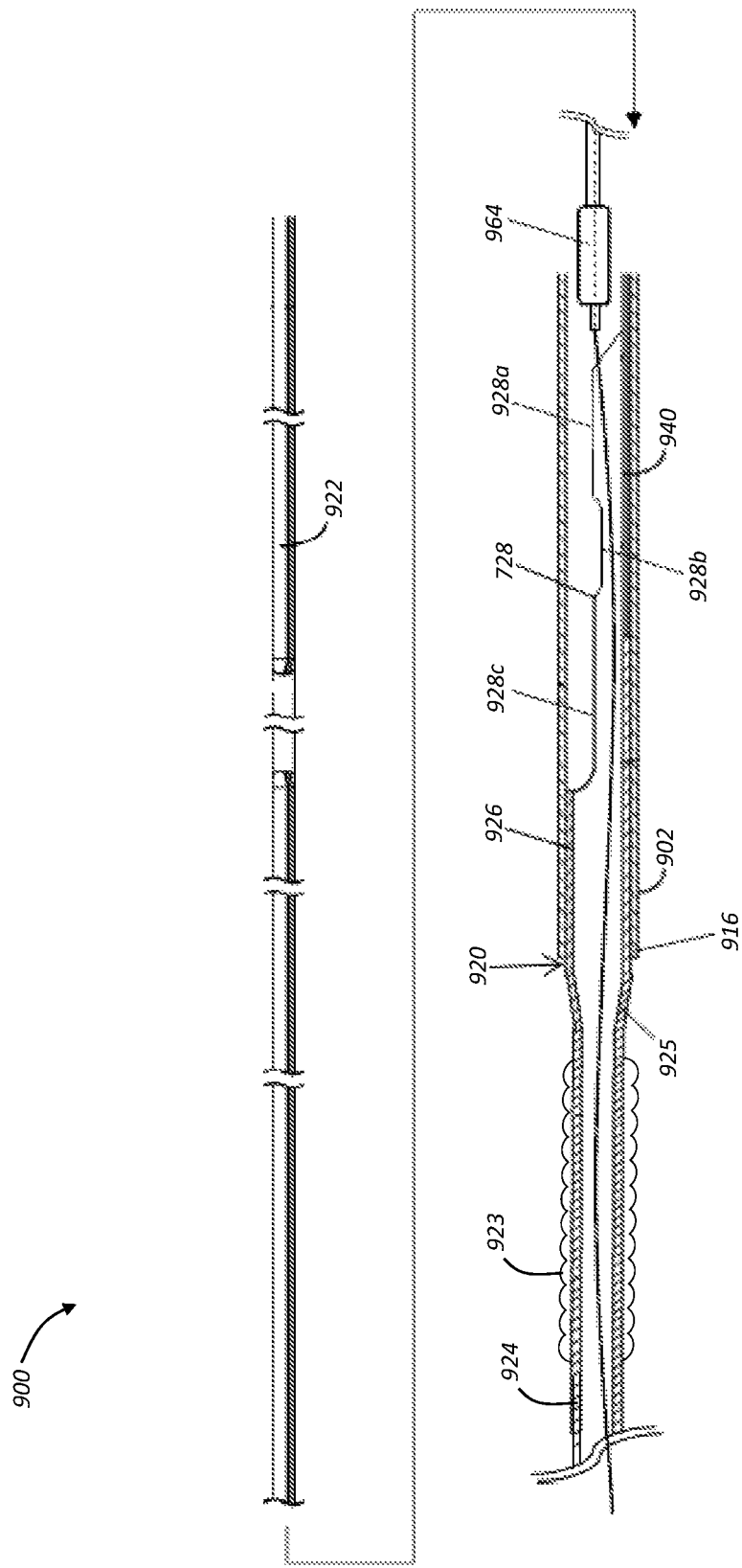
FIG. 9 illustrates a cross-sectional side view of a guide extension catheter, as constructed in accordance with at least one embodiment, and an interventional device partially within a sectioned guide catheter.

FIG. 9 illustrates a side view of an example guide extension catheter 900 positioned within a guide catheter 902 and used in conjunction with a guidewire 912 and a treating catheter 964. With the guidewire 912 and the guide catheter 902 positioned as desired, a tube member 920 of the guide extension catheter 900 can be backloaded from its narrow distal end portion 924 onto a proximal end of the guidewire 912 and advanced through a hemostasis valve coupled to the guide catheter 902. As shown, the tube member 920 of the guide extension catheter 900 can be advanced beyond a distal end 916 of the guide catheter 902 under fluoroscopy. When so arranged, portions of the tube member 920 can engage an ostium and extend within a portion of a coronary artery to help maintain the position of the guide catheter 902 as the treating catheter 964 is advanced. To firmly secure the guide extension catheter 900 from its distal end, an inflatable balloon 923 surrounds at least a portion of the distal end portion 924 of the tube member 920. Inflating the inflatable balloon 923 may be necessary where the ostium is particularly narrow and/or when significant backward force is generated during an operation. Inflating the inflatable balloon 923 may also be beneficial when only the most distal tip of the tube member's distal portion 924 can fit into a particularly narrow target vessel. In such situations, the inflatable balloon 923 may be offset from the tube member's distal tip, where it may impinge on an interior surface of a wider blood vessel. In addition, inflation of the inflatable balloon 923 may provide critical back-up support in blood vessels having irregular cross-sections, such as blood vessels lined with build-up. As further shown, embodiments of the guide extension catheter 900 can include a concave track 928, which may provide a variable degree of enclosure at portions 928a, 928b, and 928c to prevent or reduce twisting of the guidewire 912.

Figure 10A:
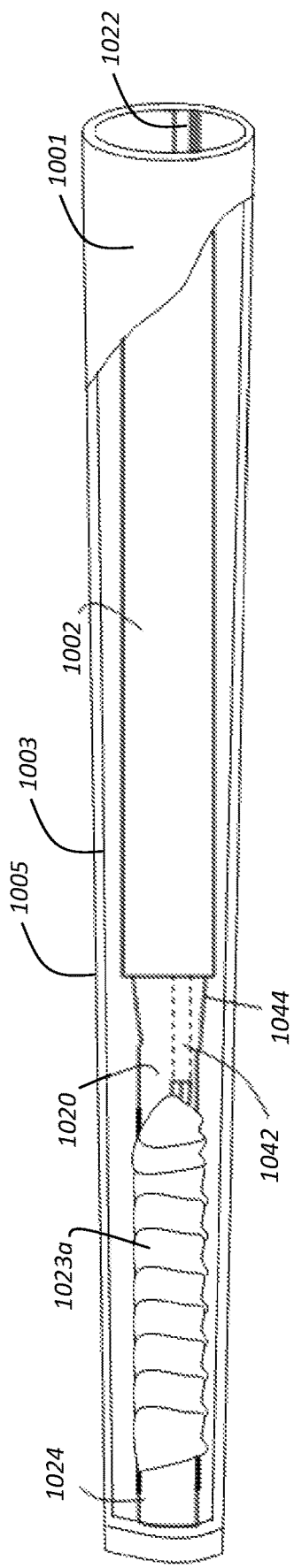
FIG. 10A illustrates an enlarged side view of a distal portion of an elongate tube member surrounded by a balloon, the balloon in a deflated configuration within a surrounding sectioned guide catheter.

FIG. 10A illustrates an enlarged side view of a distal portion 1024 of an elongate tube member 1020 surrounded by a deflated balloon 1023a within a surrounding guide catheter 1002, which has been inserted into a blood vessel 1001. As shown, the vessel 1002 includes an inner wall 1003 and an outer wall 1005. The deflated balloon 1023a may not contact the inner surface 1003 of the vessel 1001, thereby allowing the distal portion 1024 of the elongate tube 1020 to pass through the vessel.

Figure 10B:
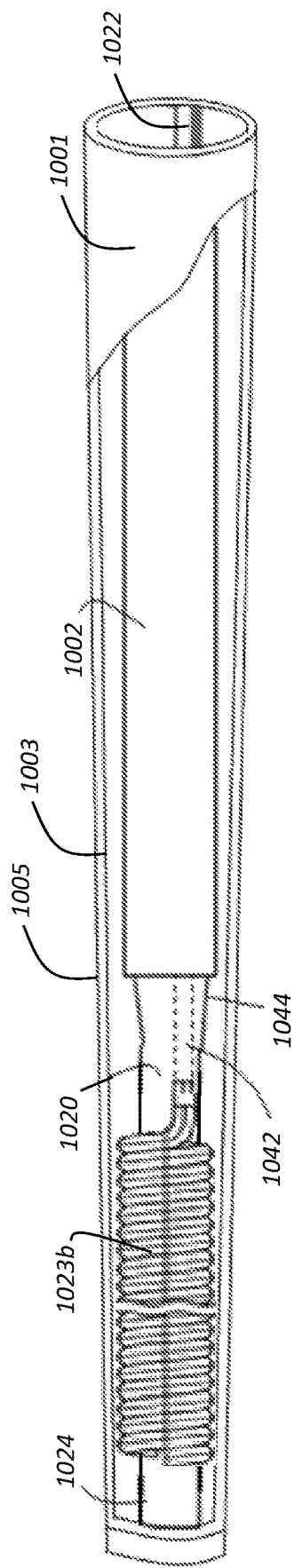
FIG. 10B illustrates an enlarged side view of a distal portion of the elongate tube member surrounded by the balloon of FIG. 10A, the balloon in an inflated configuration beyond the distal end of the guide catheter.

FIG. 10B illustrates an enlarged side view of the distal portion 1024 of the elongate tube member 1020 of FIG. 10A surrounded by an inflated balloon 1023b within the surrounding guide catheter 1002, which has been inserted into the blood vessel 1001. The inflated balloon 1023b may contact the inner surface 1003 of the vessel 1001, thereby securing the distal portion 1024 of the elongate tube 1020 at the site shown by exerting an outward radial force against the inner surface 1003.

FIG. 11A illustrates an example reinforcement member 1100, which may be included in some embodiments to increase the stiffness of the elongate tube member 1102 of a guide extension catheter (only a portion of which is shown). As described above, the reinforcement member 1100 may be sandwiched between two polymer layers constituting the elongate tube member 1102. The reinforcement member 1100 can include a plurality of longitudinal bars or strips 1104, which may be interlaced with one or more cross-bars or strips 1106. The strips 1104, 1106 may be arranged perpendicularly, or substantially perpendicularly, with respect to each other, or they may be diagonally arranged. In some examples, only the longitudinal or the cross strips may be included. The reinforcement member 1100 can extend around the entire perimeter of the elongate tube member 1102, or only a portion thereof.

FIG. 11B illustrates another example reinforcement member 1108 included with an elongate tube member 1110 (only a portion of which is shown). In this example, the reinforcement member 1108 can be comprised of spiraling bars or strips 1112, 1114, which may crisscross. In embodiments, strips in only one spiral direction, i.e., 1112 or 1114, may be included. Any suitable angle or combination of angles of the spiral with respect to the longitudinal axis of the tube may be used. Like reinforcement member 1100, reinforcement member 1108 can be sandwiched between individual layers constituting the elongate tube member 1110. The particular configuration of the reinforcement member, its location and/or length may vary in different embodiments of the guide extension catheters disclosed herein, which are not confined to examples including reinforcement members, or specific embodiments thereof. The materials constituting the reinforcement member may also vary. In examples, the reinforcement member can include stainless steel, a platinum alloy, and/or one or more polymers, for instance.

Examples

The above Detailed Description is intended to be illustrative and not restrictive. The above-described embodiments (or one or more features or components thereof) can be used in varying combinations with each other unless clearly stated to the contrary. Other embodiments can be used, such as by one of ordinary skill in the art upon reviewing the above Detailed Description. Also, various features or components have been grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment.

In Example 1, a guide extension catheter for use with a predefined length guide catheter can comprise an elongate tube member, a push member, and a balloon. The elongate tube member can have a circular cross-section with an outer diameter sized to be insertable through a cross-sectional inner diameter of the guide catheter and can define a coaxial lumen having a cross-sectional inner diameter through which an interventional cardiology device is insertable. The push member can be rigid enough to advance the elongate tube member through the guide catheter. The push member is proximal of and operably connected to the elongate tube member and can have a maximal cross-sectional dimension at a proximal portion that is smaller than the outer diameter of the elongate tube member. A combined length of the elongate tube member and the push member can be such that when at least a distal portion of the elongate tube member is extended distally of a distal end of the guide catheter, at least a portion of the proximal portion of the push member extends proximally through a hemostatic valve in common with the interventional cardiology device. The balloon can radially surround a portion of the elongate tube member and can comprise an inflatable tube coupled to an elongate shaft. The elongate shaft can include a lumen for providing inflation fluid to, or withdrawing inflation fluid from, the balloon.

In Example 2, the guide extension catheter of Example 1 can optionally be configured such that the inflatable tube is coiled in a helical manner around a central axis into a series of windings.

In Example 3, the guide extension catheter of Example 2 can optionally be configured such that adjacent windings of the inflatable tube are stacked against and bonded to each other, and an inner surface of the series of windings are bonded to an outer surface of the elongate tube member.

In Example 4, the guide extension catheter of Example 2 can optionally be configured such that adjacent windings of the inflatable tube are spaced apart, and an inner surface of the series of windings are bonded to an outer surface of the elongate tube member.

In Example 5, the guide extension catheter of any one or any combination of Examples 1-4 is optionally configured such that the elongate shaft is defined within the elongate tube member and the push member.

In Example 6, the guide extension catheter of any one or any combination of Examples 1-4 can optionally be configured such that the elongate shaft is positioned adjacent to the push member.

In Example 7, the guide extension catheter of any one or any combination of Examples 1-6 can optionally be configured such that the inflatable tube comprises two different polymer tubes.

In Example 8, the guide extension catheter of Example 7 can optionally be configured such that the two different polymer tubes include an inner tube and an outer tube, and the polymer of the inner tube has a higher melting temperature than the polymer of the outer tube.

In Example 9, the guide extension catheter of any one or any combination of Examples 1-8 can optionally further comprise a bioactive layer coating an outer surface of the balloon.

In Example 10, the guide extension catheter of Example 9 can optionally be configured such that the bioactive layer includes one or more drugs, therapeutic agents, diagnostic agents, or combinations thereof.

In Example 11, the guide extension catheter of Example 9 can optionally be configured such that the bioactive layer includes one or more drugs and one or more excipients.

In Example 12, the guide extension catheter of any one or any combination of Examples 1-11 can optionally be configured such that the elongate tube member includes a flexible cylindrical distal tip portion and a flexible cylindrical portion with a reinforcement member that is proximal to the flexible cylindrical distal tip portion.

In Example 13, the guide extension catheter of any one or any combination of Examples 1-12 can optionally be configured such that the proximal portion of the elongate tube member comprises structure defining a proximal side opening extending for a distance along the longitudinal axis, and accessible from a longitudinal side defined transverse to the longitudinal axis, to receive the interventional cardiology device into the coaxial lumen while the proximal portion remains within the lumen of the guide catheter.

In Example 14, the guide extension catheter of Example 13 can optionally be configured such that the proximal side opening defines a concave track configured to guide the interventional cardiology device along a length of the concave track.

In Example 15, a method can comprise advancing a distal end of a predefined length guide catheter having a continuous lumen through a blood vessel to an ostium of a coronary artery; advancing a distal end of a guide extension catheter through, and beyond the distal end of, the guide catheter, including advancing a push member of the guide extension catheter that is proximal of, operably connected to, and more rigid along a longitudinal axis than an elongate tube member of the guide extension catheter, into the continuous lumen of the guide catheter, the push member having a maximal cross-sectional dimension at a proximal portion that is smaller than a cross-sectional outer diameter of the elongate tube member and having a length such that, when combined with the length of the elongate tube member, a distal end portion of the elongate tube member is extendable through the continuous lumen of the guide catheter and beyond the distal end of the guide catheter while a proximal end of the push member is extendable through a hemostatic valve positioned at a proximal end of the guide catheter, the advancement of the push member causing advancement of the distal end portion of the elongate tube member beyond the distal end of the guide catheter while a side opening of the guide extension catheter remains within the continuous lumen of the guide catheter, the side opening extending for a distance along a longitudinal axis of the guide extension catheter and accessible from a longitudinal side defined transverse to the longitudinal axis, the elongate tube member defining a lumen coaxial with the continuous lumen of the guide catheter and having a cross-sectional inner diameter through which an interventional cardiology device is insertable; and inflating a balloon, which radially surrounds a portion of the elongate tube member, to engage the elongate tube member with an inner surface of the coronary artery or the guide catheter, including urging fluid through a lumen of an elongate shaft and into the balloon to inflate a series of helical windings of the balloon.

In Example 16, the method of Example 15 can optionally be configured such that the elongate shaft is defined within the elongate tube member and the push member.

In Example 17, the method of any one of Examples 15 or 16 can optionally be configured such that inflating the balloon includes engaging the elongate tube member with the inner surface of the guide catheter.

In Example 18, the method of any one or any combination of Examples 15-17 can optionally be configured such that advancing the distal end of the guide extension catheter through, and beyond the distal end of, the guide catheter includes sealing around the push member and the elongate shaft with the hemostatic valve positioned at the proximal end of the guide catheter.

In Example 19, the method of any one or any combination of Examples 15-18 can optionally further comprise maintaining the balloon in the inflated configuration and releasing a bioactive layer, which is coated on an outer surface of the balloon, into the inner surface of the coronary artery.

In Example 20, the method of Example 19 can optionally be configured such that maintaining the balloon in the inflated configuration includes maintaining the balloon in the inflated configuration for more than 60 seconds.

In Example 21, the method of any one or any combination of Examples 15-20 can optionally further comprising maintaining the distal end portion of the elongate tube member in position beyond the distal end of the guide catheter; and while maintaining the distal end portion of the elongate tube member is positioned beyond the distal end of the guide catheter, advancing a balloon catheter or stent at least partially through the continuous lumen of the guide catheter, into the side opening and through the coaxial lumen of the elongate tube member, and into the coronary artery.

Closing Notes:

The above Detailed Description includes references to the accompanying drawings, which form a part of the Detailed Description. The Detailed Description should be read with reference to the drawings. The drawings show, by way of illustration, specific embodiments in which the present guide extension catheters and related methods can be practiced. These embodiments are also referred to herein as "examples."

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art considers equivalent to the recited value (i.e., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to an operating physician. "Distal" and "distally" refer to a position that is distant from, or in a direction away from, the physician. "Proximal" and "proximally" refer to a position that is near, or in a direction toward, the physician. And the term "interventional device (s)" is used to include, but is not limited to, guidewires, balloon catheters, stents and stent catheters.

The scope of the present guide extension catheters and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A guide extension catheter for use with a predefined length guide catheter, the guide extension catheter comprising:
   an elongate tube member having a circular cross-section with an outer diameter sized to be insertable through a cross-sectional inner diameter of the guide catheter and defining a coaxial lumen having a cross-sectional inner diameter through which an interventional cardiology device is insertable;
   a push member configured to advance the elongate tube member through the guide catheter, the push member being proximal of and operably connected to the elongate tube member, the push member having a maximal cross-sectional dimension at a proximal portion that is smaller than the outer diameter of the elongate tube member and having a length that when combined with a length of the elongate tube member forms a device length that is longer than the guide catheter, such that when at least a distal portion of the elongate tube member is extended distally of a distal end of the guide catheter, at least a portion of the proximal portion of the push member extends proximally through a hemostatic valve in common with the interventional cardiology device; and
   a balloon radially surrounding a portion of the elongate tube member, the balloon comprising an inflatable tube in fluid communication with an elongate lumen configured to provide inflation fluid to, or withdraw inflation fluid from, the balloon, wherein the inflatable tube is coiled in a helical manner around a central axis into a series of windings.

2. The guide extension catheter of claim 1, wherein adjacent windings of the inflatable tube are stacked against and bonded to each other, and an inner surface of the series of windings are bonded to an outer surface of the elongate tube member.

3. The guide extension catheter of claim 1, wherein adjacent windings of the inflatable tube are spaced apart such that a lateral space is defined between them, and an inner surface of the series of windings are bonded to an outer surface of the elongate tube member.

4. The guide extension catheter of claim 1, wherein the inflatable tube comprises two different polymer tubes.

5. The guide extension catheter of claim 4, wherein the two different polymer tubes include an inner tube and an outer tube, and the polymer of the inner tube has a higher melting temperature than the polymer of the outer tube.

6. The guide extension catheter of claim 1, further comprising a bioactive layer coating an outer surface of the balloon.

7. The guide extension catheter of claim 6, wherein the bioactive layer includes one or more drugs, therapeutic agents, diagnostic agents, or combinations thereof.

8. The guide extension catheter of claim 6, wherein the bioactive layer includes one or more drugs and one or more excipients.

9. The guide extension catheter of claim 1, wherein the elongate tube member includes a flexible cylindrical distal tip portion and a flexible cylindrical portion with a reinforcement member that is proximal to the flexible cylindrical distal tip portion.

10. A guide extension catheter for use with a predefined length guide catheter, the guide extension catheter comprising:
    an elongate tube member having a circular cross-section with an outer diameter sized to be insertable through a cross-sectional inner diameter of the guide catheter and defining a coaxial lumen having a cross-sectional inner diameter through which an interventional cardiology device is insertable, wherein a proximal portion of the elongate tube member comprises structure defining a proximal side opening extending for a distance along a longitudinal axis, and accessible from a longitudinal side defined transverse to the longitudinal axis, to receive the interventional cardiology device into the coaxial lumen while the proximal portion remains within a lumen of the guide catheter;
    a push member configured to advance the elongate tube member through the guide catheter, the push member being proximal of and operably connected to the elongate tube member, the push member having a maximal cross-sectional dimension at a proximal portion that is smaller than the outer diameter of the elongate tube member and having a length that when combined with a length of the elongate tube member forms a device length that is longer than the guide catheter, such that when at least a distal portion of the elongate tube member is extended distally of a distal end of the guide catheter, at least a portion of the proximal portion of the push member extends proximally through a hemostatic valve in common with the interventional cardiology device; and a balloon radially surrounding a portion of the elongate tube member, the balloon comprising an inflatable tube in fluid communication with an elongate lumen configured to provide inflation fluid to, or withdraw inflation fluid from, the balloon.

11. The guide extension catheter of claim 10, wherein the proximal side opening defines a concave track configured to guide the interventional cardiology device along a length of the concave track.

12. The guide extension catheter of claim 10, wherein the inflatable tube comprises two different polymer tubes.

13. The guide extension catheter of claim 10, further comprising a bioactive layer coating an outer surface of the balloon.

14. The guide extension catheter of claim 10, wherein the elongate tube member includes a flexible cylindrical distal tip portion and a flexible cylindrical portion with a reinforcement member that is proximal to the flexible cylindrical distal tip portion.

15. A method, comprising:
advancing a distal end of a predefined length guide catheter having a continuous lumen through a blood vessel to an ostium of a coronary artery;
advancing a distal end of a guide extension catheter through, and beyond the distal end of, the guide catheter, including advancing a push member of the guide extension catheter that is proximal of, operably connected to, and more rigid along a longitudinal axis than an elongate tube member of the guide extension catheter, into the continuous lumen of the guide catheter, the push member having a maximal cross-sectional dimension at a proximal portion that is smaller than a cross-sectional outer diameter of the elongate tube member and having a length such that, when combined with the length of the elongate tube member, a distal end portion of the elongate tube member is extendable through the continuous lumen of the guide catheter and beyond the distal end of the guide catheter while a proximal end of the push member is extendable through a hemostatic valve positioned at a proximal end of the guide catheter, the advancement of the push member causing advancement of the distal end portion of the elongate tube member beyond the distal end of the guide catheter while a side opening of the guide extension catheter remains within the continuous lumen of the guide catheter, the side opening extending for a distance along a longitudinal axis of the guide extension catheter and accessible from a longitudinal side defined transverse to the longitudinal axis, the elongate tube member defining a lumen coaxial with the continuous lumen of the guide catheter and having a cross-sectional inner diameter through which an interventional cardiology device is insertable; and inflating a balloon, which radially surrounds a portion of the elongate tube member, to engage the elongate tube member with an inner surface of the guide catheter, including urging fluid into the balloon to inflate a series of helical windings of the balloon.

16. The method, of claim 15, wherein urging fluid into the balloon to inflate the series of helical windings of the balloon includes urging fluid through a lumen of an elongate shaft, which is defined within the elongate tube member and the push member.

17. The method of claim 16, wherein advancing the distal end of the guide extension catheter through, and beyond the distal end of, the guide catheter includes sealing around the push member and the elongate shaft with the hemostatic valve positioned at the proximal end of the guide catheter.

18. The method of claim 15, further comprising maintaining the balloon in an inflated configuration and releasing a bioactive layer, which is coated on an outer surface of the balloon, into an inner surface of the coronary artery.

19. The method of claim 18, wherein maintaining the balloon in the inflated configuration includes maintaining the balloon in the inflated configuration for more than 60 seconds.

20. The method of claim 15, further comprising:
maintaining the distal end portion of the elongate tube member in position beyond the distal end of the guide catheter; and
while maintaining the distal end portion of the elongate tube member is positioned beyond the distal end of the guide catheter, advancing a balloon catheter or stent at least partially through the continuous lumen of the guide catheter, into the side opening and through the coaxial lumen of the elongate tube member, and into the coronary artery.

* * * * *